(12) United States Patent
Iketani et al.

(10) Patent No.: US 10,399,057 B2
(45) Date of Patent: Sep. 3, 2019

(54) ANALYSIS DEVICE, GENETIC ANALYSIS METHOD, ANALYSIS RECEPTACLE, AND CONTROL METHOD FOR FUZZY CONTROL

(71) Applicant: PHC Holdings Corporation, Minato-ku, Tokyo (JP)

(72) Inventors: Seiichiro Iketani, Ehime (JP); Takashi Ochi, Ehime (JP); Ryuji Shimizu, Ehime (JP); Masahiro Kouge, Ehime (JP); Shinichi Nakasuka, Ehime (JP); Kazuyoshi Mori, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 186 days.

(21) Appl. No.: 14/764,980

(22) PCT Filed: Feb. 4, 2014

(86) PCT No.: PCT/JP2014/000594
§ 371 (c)(1),
(2) Date: Jul. 30, 2015

(87) PCT Pub. No.: WO2014/122924
PCT Pub. Date: Aug. 14, 2014

(65) Prior Publication Data
US 2015/0367314 A1    Dec. 24, 2015

(30) Foreign Application Priority Data

Feb. 5, 2013   (JP) .................................. 2013-020144
Feb. 15, 2013  (JP) .................................. 2013-027416
(Continued)

(51) Int. Cl.
*B01L 3/00*   (2006.01)
*C12M 3/00*   (2006.01)
(Continued)

(52) U.S. Cl.
CPC ............ *B01J 19/0013* (2013.01); *B01L 7/00* (2013.01); *C12Q 1/68* (2013.01);
(Continued)

(58) Field of Classification Search
CPC ...... C12M 41/14; C12M 41/12; C12M 41/20; B01L 7/00; B01L 7/52
See application file for complete search history.

(56) References Cited

U.S. PATENT DOCUMENTS 4,689,303 A * 8/1987 Kraft ......................... B01L 7/00
                                                      126/21 A
5,455,175 A * 10/1995 Wittwer .................... B01L 7/52
                                                        422/417
(Continued)

FOREIGN PATENT DOCUMENTS

JP   H06-214612 A   8/1994
JP   H08-210688 A   8/1996
(Continued)

OTHER PUBLICATIONS

International Search Report dated Apr. 22, 2014 for PCT Appln No. PCT/JP2014/000594.

*Primary Examiner* — Nathan A Bowers
(74) *Attorney, Agent, or Firm* — Wenderoth, Lind & Ponack, L.L.P.

(57) ABSTRACT

With this analysis device, air that has been heated by a heater is blown by a fan in the direction of an analysis receptacle rotary driver and an analysis receptacle that is rotationally driven by the analysis receptacle rotary driver. The analysis receptacle rotary driver rotates the analysis receptacle within the analysis chamber in the same direction as the direction of air flow produced by the fan.

3 Claims, 43 Drawing Sheets

(30) Foreign Application Priority Data

| Feb. 15, 2013 | (JP) | 2013-027417 |
| Feb. 15, 2013 | (JP) | 2013-027418 |
| Feb. 15, 2013 | (JP) | 2013-027419 |
| Feb. 15, 2013 | (JP) | 2013-027420 |
| Jan. 16, 2014 | (JP) | 2014-006101 |

(51) Int. Cl.

| B01J 19/00 | (2006.01) |
| G01N 35/00 | (2006.01) |
| B01L 7/00 | (2006.01) |
| C12Q 1/68 | (2018.01) |

(52) U.S. Cl.

CPC ............. G01N 35/00069 (2013.01); *B01J 2219/00054* (2013.01); *B01L 2300/0803* (2013.01); *B01L 2300/1844* (2013.01); *B01L 2400/0409* (2013.01); *G01N 2035/00356* (2013.01)

(56) References Cited

U.S. PATENT DOCUMENTS

| 5,921,099 | A | 7/1999 | Lee |
| 6,706,519 | B1 | 3/2004 | Kellogg et al. |
| 8,303,908 | B2 | 11/2012 | Taguchi et al. |
| 9,346,054 | B2 * | 5/2016 | Chun .................. B01L 7/5255 |
| 2006/0008381 | A1 | 1/2006 | Taguchi et al. |
| 2006/0073584 | A1 | 4/2006 | Sasaki et al. |
| 2009/0022625 | A1 * | 1/2009 | Lee .......................... B01L 7/52 |
| | | | 422/68.1 |
| 2009/0035847 | A1 * | 2/2009 | Cho .................. B01F 11/0002 |
| | | | 435/289.1 |

FOREIGN PATENT DOCUMENTS

| JP | H10-002875 A | 1/1998 |
| JP | H10-333754 A | 12/1998 |
| JP | 2004-150804 A | 5/2004 |
| JP | 3623479 B2 | 2/2005 |
| JP | 2006-122041 A | 5/2006 |
| JP | 2006-300802 A | 11/2006 |
| JP | 2008-278783 A | 11/2008 |
| JP | 4281877 B2 | 6/2009 |
| JP | 2012-127882 A | 7/2012 |
| WO | 1997/046712 A2 | 12/1997 |
| WO | 2000/078455 A1 | 12/2000 |
| WO | WO-2012036341 A1 * | 3/2012 |

\* cited by examiner

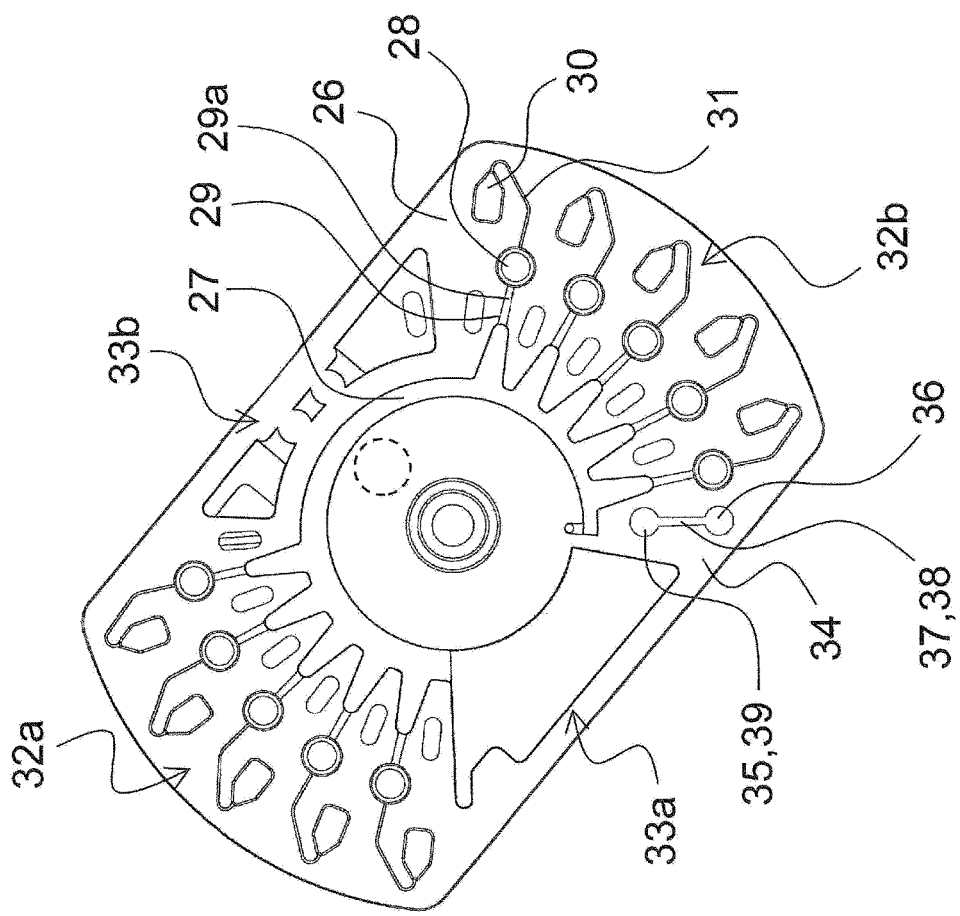

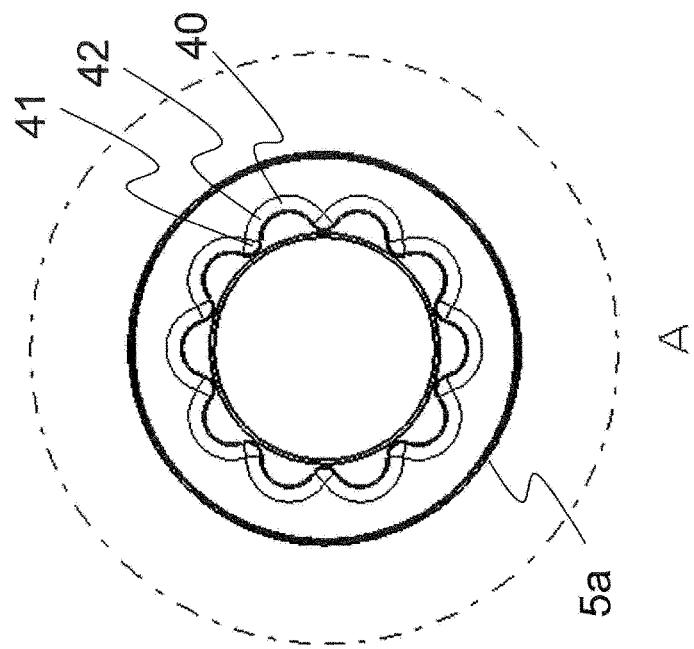
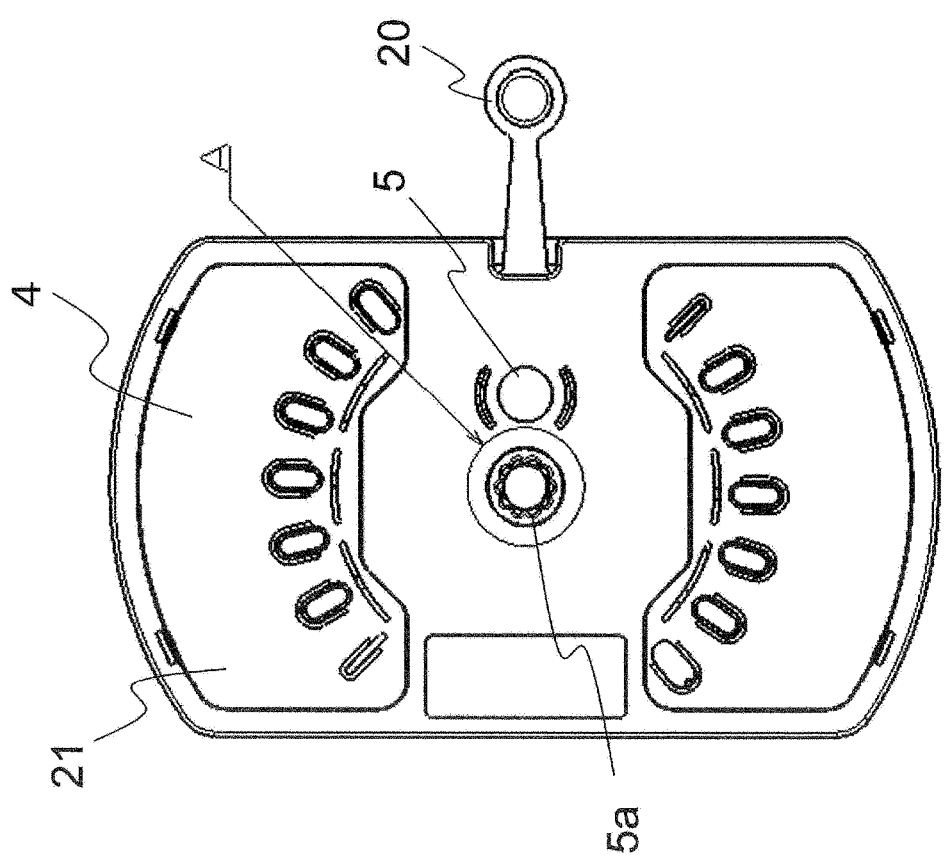
FIG. 22B
FIG. 22A

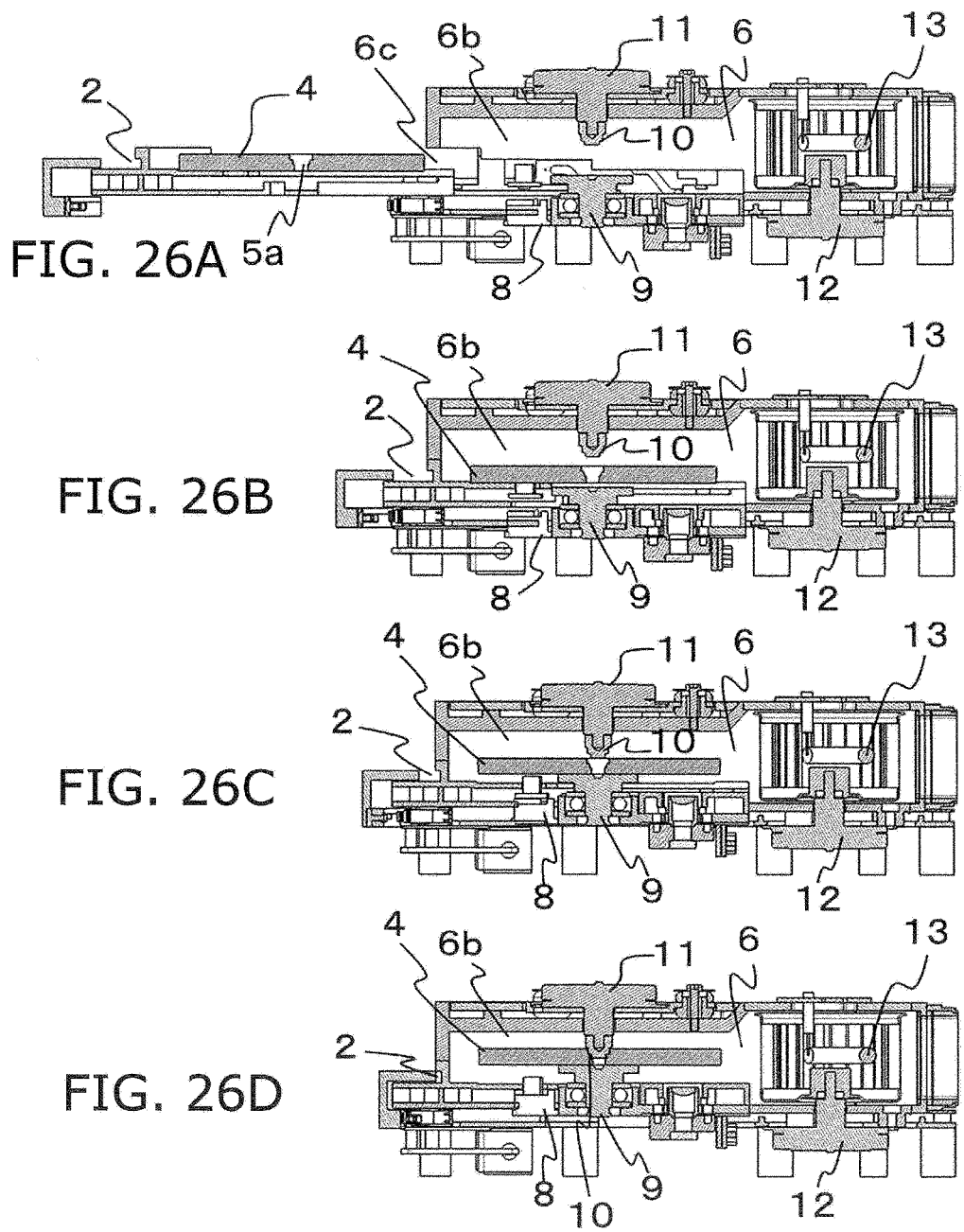

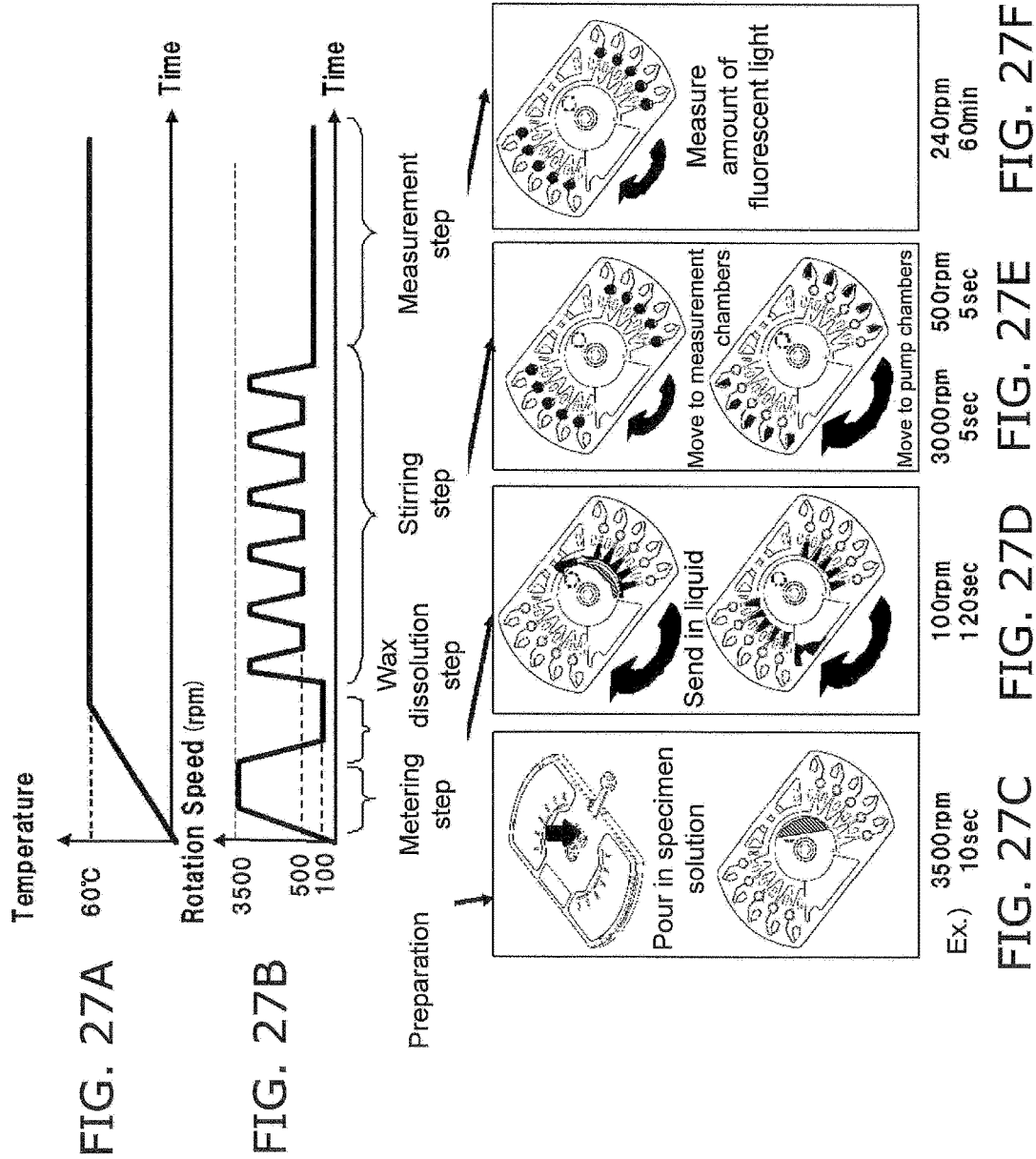

| ΔE \ E | NB | NS | ZO | PS | PB |
|---|---|---|---|---|---|
| NB | NB | NB | NB | NS | PB |
| NS | NB | NB | NS | ZO | PS |
| ZO | NB | NS | ZO | PS | PB |
| PS | NS | ZO | PS | PS | PB |
| PB | ZO | PS | PS | PB | PB |

FIG. 34

ANALYSIS DEVICE, GENETIC ANALYSIS METHOD, ANALYSIS RECEPTACLE, AND CONTROL METHOD FOR FUZZY CONTROL

PRIORITY

This is a National Stage Application under 35 U.S.C. § 365 of International Application PCT/JP2014/000594, with an international filing date of Feb. 4, 2014, which claims priority to Japanese Patent Application No. 2013-020144 filed on Feb. 5, 2013, Japanese Patent Application No. 2013-027416 filed on Feb. 15, 2013, Japanese Patent Application No. 2013-027417 filed on Feb. 15, 2013, Japanese Patent Application No. 2013-027418 filed on Feb. 15, 2013, Japanese Patent Application No. 2013-027419 filed on Feb. 15, 2013, Japanese Patent Application No. 2013-027420 filed on Feb. 15, 2013, and Japanese Patent Application No. 2014-006101 filed on Jan. 16, 2014. The entire disclosures of International Application PCT/JP2014/000594, Japanese Patent Application No. 2013-020144, Japanese Patent Application No. 2013-027416, Japanese Patent Application No. 2013-027417, Japanese Patent Application No. 2013-027418, Japanese Patent Application No. 2013-027419, Japanese Patent Application No. 2013-027420 and Japanese Patent Application No. 2014-006101 are hereby incorporated herein by reference.

TECHNICAL FIELD

Certain implementations of present invention relate to a genetic analysis method, analysis receptacle, and control method for fuzzy control, with which the analysis of genes and the like is performed.

BACKGROUND

A conventional analysis device comprised an analysis chamber, a fan provided inside the analysis chamber, a heating means for heating air blown by the fan, and an analysis receptacle support means that was disposed at a specific spacing in the analysis chamber in the blowing direction of the fan.

Specifically, with a conventional configuration, warm air heated by the heating means was blown toward the analysis receptacle in the analysis chamber, and the temperature of the analysis receptacle was thereby controlled to be a target temperature. This improved analysis accuracy by maintaining a steady analysis environment.

A problem encountered with the above-mentioned conventional configuration was diminished analysis accuracy.

Specifically, with the above-mentioned conventional configuration, warm air from the fan was blown directly against the analysis receptacle. However, since there is temperature unevenness in the warm air blown out from the fan, there ends up being temperature unevenness in the analysis receptacle portion. As a result, it can be difficult to hold the analysis environment at a steady target temperature, and there is the risk that the analysis accuracy of the analysis device will be diminished.

It is an object of certain implementations to provide an analysis device with which analysis accuracy can be enhanced.

Also, with a conventional genetic analysis method, to identify whether or not a particular gene is present, a gene amplification means was used to react a specimen with a reagent containing a substance in which a fluorescent reagent is bonded to a primer that undergoes a specific reaction with a particular gene sequence. Whether or not the particular gene was present was determined from whether or not the intensity of fluorescent light of the fluorescent reagent that undergoes a specific reaction with the particular gene is greater than a specific value.

With the above-mentioned conventional configuration, however, since the presence of a particular gene is determined from whether or not the intensity of fluorescent light of a fluorescent reagent that undergoes a specific reaction with a particular gene is greater than a specific value, the intensity of the fluorescent light must be observed after a specific length of time has elapsed. The analysis thus takes a long time.

It is an object of certain implementations to provide a genetic analysis method with which analysis time can be shortened.

Also, a conventional analysis receptacle comprised a main case, a rotary shaft insertion hole that was provided in the center of the main case and into which a rotary shaft was inserted, and a reaction component provided around a circle whose center was the rotary shaft insertion hole.

A configuration is used in which the temperature of the reaction component is brought closer to the target temperature by performing control such that warm air heated by the heating means directly hits the analysis receptacle, and the temperature of a portion of the analysis receptacle reaches the target temperature. Consequently, the analysis environment can be optimized and analysis accuracy improved.

Nevertheless, with the above-mentioned conventional configuration, the warm air from the fan is blown directly onto the surface of the main case of the analysis receptacle. Since the main case has a thermal capacity, it is difficult to match the temperature of the main case to that of the reaction component. As a result, there is the risk that there will be a large difference between the temperature of the reaction component and the target temperature, which would lower the analysis accuracy.

It is an object of certain implementations to provide an analysis device with which analysis accuracy can be improved.

Also, a conventional analysis device comprised a disk-shaped main case, a rotary shaft insertion hole that was provided in the center of the main case and into which a rotary shaft was inserted, and a reaction component provided around a circle whose center was the rotary shaft insertion hole.

With this analysis receptacle, the rotary shaft provided to the measurement chamber of the analysis device was inserted and rotated, and warm air from the fan was blown directly onto the surface of the main case of the rotating analysis device. Consequently, analysis of a specimen was performed under an environment of the target temperature.

However, with the above-mentioned conventional configuration, the warm air from the fan is blown directly onto the surface of the main case of the rotating analysis receptacle, and since the main case here is disk-shaped, the measurement chamber is separated on the upper face side and the lower face side of the analysis receptacle, air circulation is poor, and a temperature differential results. As a result, a difference from the target temperature occurs in the reaction component of the analysis receptacle, so there is the risk that analysis accuracy will be diminished.

It is an object of certain implementations to provide an analysis device with which analysis accuracy can be improved.

Also, with a conventional fuzzy control method, fuzzy sets were produced for deviation, deviation rate, and output, and temperature control, etc., was performed on the basis of these fuzzy sets.

For response that could not be remedied by fuzzy control alone, such as increasing response speed, fuzzy control was combined with conventional PI control to improve fuzzy control.

The problem with the conventional example mentioned above was response instability due to the temperature state in then ambient environment.

Specifically, depending on the temperature state in then ambient environment of a temperature control device, there is that the risk that overshooting will occur, or that it will take too long to reach the target temperature, thereby resulting in response instability.

In particular, there has recently been a need to reach the target temperature in a genetic analysis device quickly and stably, without any overshoot.

This is because the reaction of the reagent used for genetic analysis only proceeds properly near the target temperature, so below the target temperature it is important to leave a transient state and reach the target temperature quickly. Furthermore, it is important not to go over the target temperature (that is, not to overshoot), so there has been a need for stable response characteristics regardless of the temperature state of the ambient environment of a temperature control device.

In view of this, it is an object of certain implementations to provide a control method for fuzzy control with which stable response characteristics can be obtained regardless of the temperature state of the ambient environment, as well as a temperature control device and a genetic analysis device that make use of this method.

SUMMARY

To achieve the stated object, certain implementations comprise an analysis chamber, a fan, a heater, and an analysis receptacle rotary driver. An analysis receptacle is placed inside the analysis chamber. The fan is provided inside the analysis chamber and blows air at the analysis receptacle. The heater heats the air blown from the fan toward the analysis receptacle. The analysis receptacle rotary driver is disposed a specific distance away from the fan in the blowing direction of the fan inside the analysis chamber, and rotates the analysis receptacle in the same direction as the direction of air flow formed by the fan.

As discussed above, with certain implementations, the rotation direction of the analysis receptacle that is rotated by the analysis receptacle rotary driver is the same as the direction of the air flow formed by the fan. Therefore, the air is stirred at the portion where the analysis receptacle and the air flow come into contact. As a result, temperature unevenness is extremely low at the portion where the analysis receptacle and the air flow come into contact, so analysis accuracy can be enhanced.

The genetic analysis method pertaining to the second invention is a method in which a gene amplifier is used to subject a specimen to amplification processing, and the specimen is reacted with a reagent containing a substance in which a fluorescent reagent is bonded to a primer that undergoes a specific reaction with a particular gene sequence, to identify whether that particular gene is present, said method comprising an amplification step and a determination step. The amplification step involves subjecting the specimen to amplification processing of the particular gene. The determination step involves determining whether or not a particular gene is present, after the amplification step, based on whether or not a differential value for the intensity of fluorescent light of the fluorescent reagent that undergoes a specific reaction with the particular gene is above a specific threshold.

With the second invention, the differential values for the change in intensity of the fluorescent light of the fluorescent reagent that undergoes a specific reaction with a particular gene are successively observed to determine whether or not the gene is present, so the presence of a particular gene can be identified immediately in response to the amount of change in the gene. Thus, analysis time can be shortened over that in the past.

The analysis receptacle pertaining to the third invention comprises a main case, a rotary shaft insertion hole, a reaction component, an intake opening, and a discharge opening. The rotary shaft insertion hole is provided in the center portion of the main case, and a rotary shaft is inserted into it. The reaction component is provided around a circle inside the main case and centered on the rotary shaft insertion hole. The intake opening is provided on the inner peripheral side of the reaction component. The discharge opening is provided on the outer peripheral side of the reaction component.

With the third invention, the intake opening is provided on the inner peripheral side of the reaction component of the main case, and the discharge opening on the outer peripheral side of the reaction component. Therefore, when the main case rotates around the rotary shaft, the negative pressure generated in the rotary shaft portion causes heated air to be drawn into the main case from the outside of the main case. After this, the heated air passes the outer periphery of the reaction component, and is then discharged from the discharge opening to outside the main case. Consequently, the temperature of the reaction component can be kept at the set temperature by allowing the temperature-controlled heated air to pass directly through the outer periphery of the reaction component. As a result, analysis accuracy is better than in the past.

The analysis receptacle pertaining to the fourth invention comprises a main case, a rotary shaft insertion hole, a reaction component, a first region, and a second region. The rotary shaft insertion hole is provided in the center of the main case. The reaction component is provided around a circle centered on the rotary shaft insertion hole. The first region is disposed inside the main case at a position that is a first distance away from the rotational axis center. The second region is disposed inside the main case at a position whose distance from the rotational axis center is shorter than the first distance.

With the fourth invention, in a state in which warm air from the fan is blown directly at the surface of the main case of the rotating analysis receptacle, the main case becomes non-disk-shaped, and in the second region, which is at a shorter distance from the rotational axis center, air circulation occurs on the upper and lower sides of the analysis receptacle, which stirs the air. Thus, temperature unevenness can be kept to a minimum at the upper face and lower face of the analysis receptacle. As a result, the reaction component of the analysis receptacle can be efficiently maintained near the target temperature, and this improves analysis accuracy.

The control method for fuzzy control pertaining to the fifth invention is a method having ZO, PS (positive small), and PB (positive big) fuzzy sets of deviation, said method comprising a first step and a second step. The first step involves monitoring the time axis response and deciding whether or not an overshoot value has exceeded a specific value, or whether or not the response speed of a response value is at least a specific time. The second step involves multiplying the fuzzy sets ZO, PS, and PB in which the X axis of the fuzzy sets of deviation is in the positive quadrant, by a specific scaling factor for X values of vertex coordinates of fuzzy sets in which the grade is 0 or 1, and updating the fuzzy sets as new fuzzy sets.

With the fifth invention, it is decided whether or not an overshoot value has exceeded a specific value, or whether or not the response speed of a response value is at least a specific time, and the response characteristics can be updated in the direction of improvement according to the decision result, so in the next control more stable response characteristics can be obtained.

BRIEF DESCRIPTION OF THE DRAWINGS

FIG. 21 is a plan view of the main parts of the analysis receptacle in an embodiment of the present invention;

FIGS. 22A and 22B are a plan view and a detail view of the main parts of the analysis receptacle in an embodiment of the present invention;

FIGS. 25A and 25C are exploded oblique views of the main parts of the genetic analysis device in an embodiment of the present invention, while

FIGS. 26A to 26D are cross sections of the main parts of the genetic analysis device in an embodiment of the present invention;

FIGS. 27A to 27F is a step diagram of the genetic analysis device in an embodiment of the present invention;

FIG. 34 shows fuzzy rules in the temperature control method in an embodiment of the present invention;

DETAILED DESCRIPTION

The genetic analysis device (analysis device) pertaining to an embodiment of the present invention will now be described through reference to the appended drawings.

As shown in FIGS. 1 to 6, with the genetic analysis device in this embodiment, an opening 3 from which an analysis receptacle loading tray 2 moves in and out is provided to the front face of a main case 1.

Figure 1:
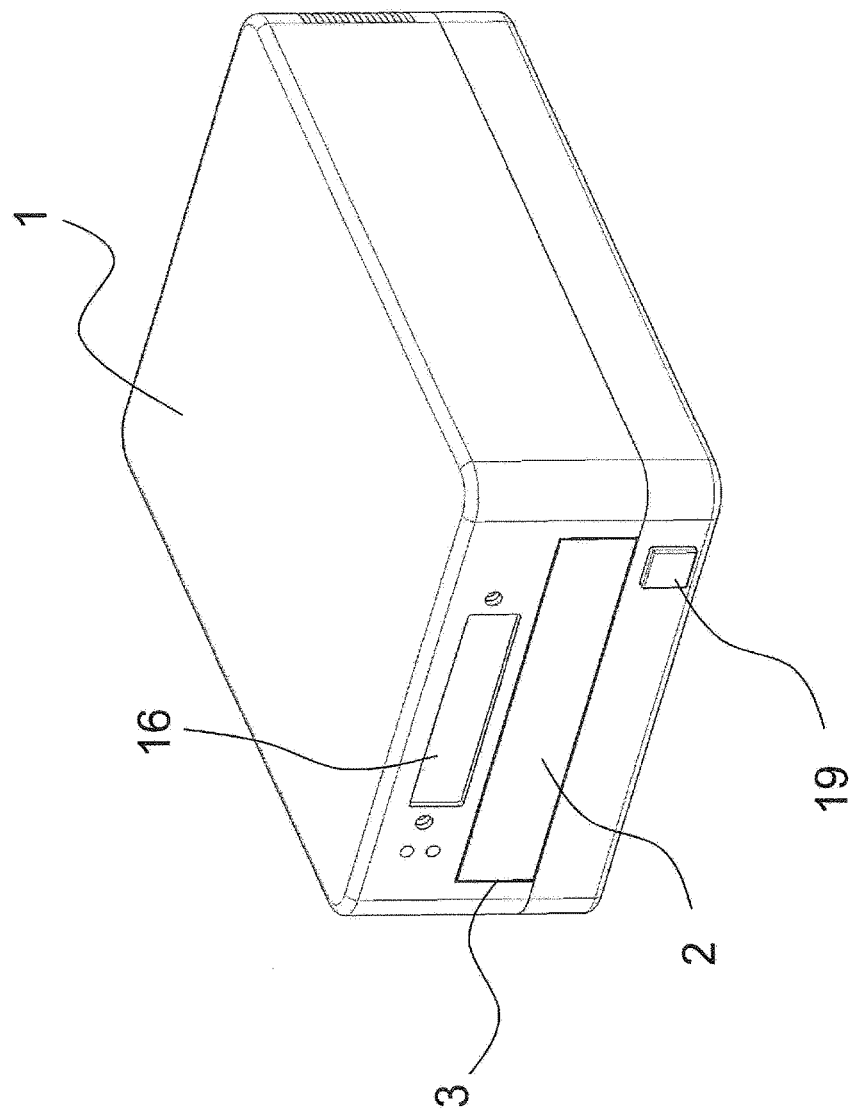
FIG. 1 is an oblique view of the genetic analysis device in an embodiment of the present invention.
Figure 2:
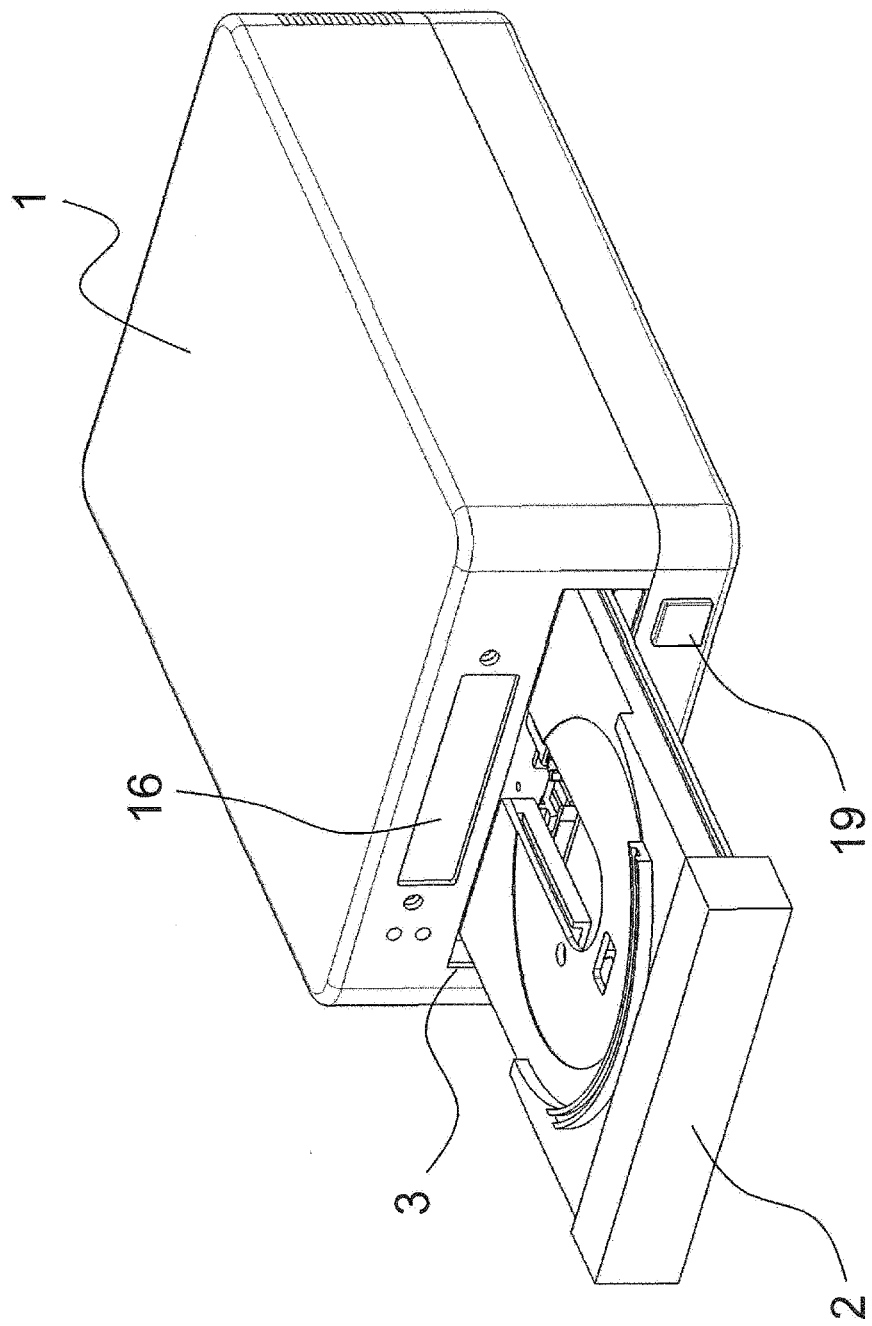
FIG. 2 is an oblique view of the genetic analysis device in an embodiment of the present invention.
Figure 3:
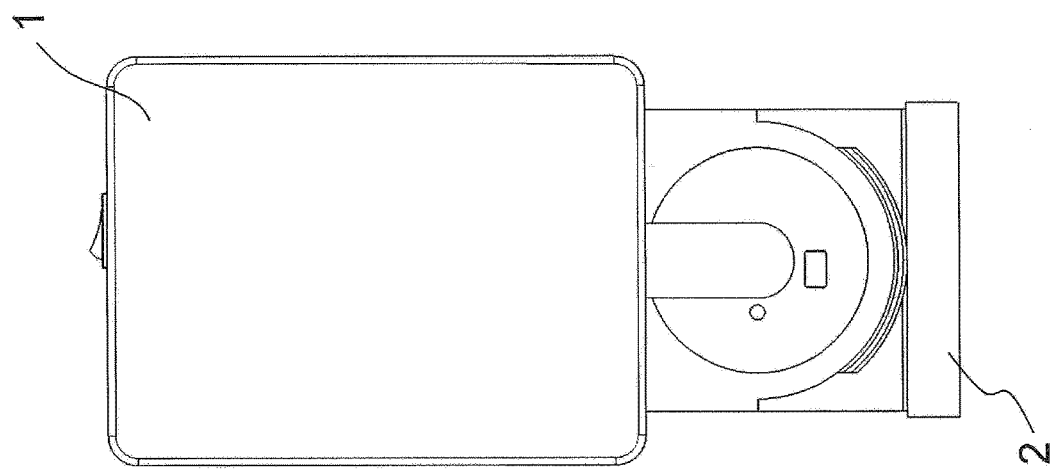
FIG. 3 is a plan view of the genetic analysis device in an embodiment of the present invention.
Figure 4:
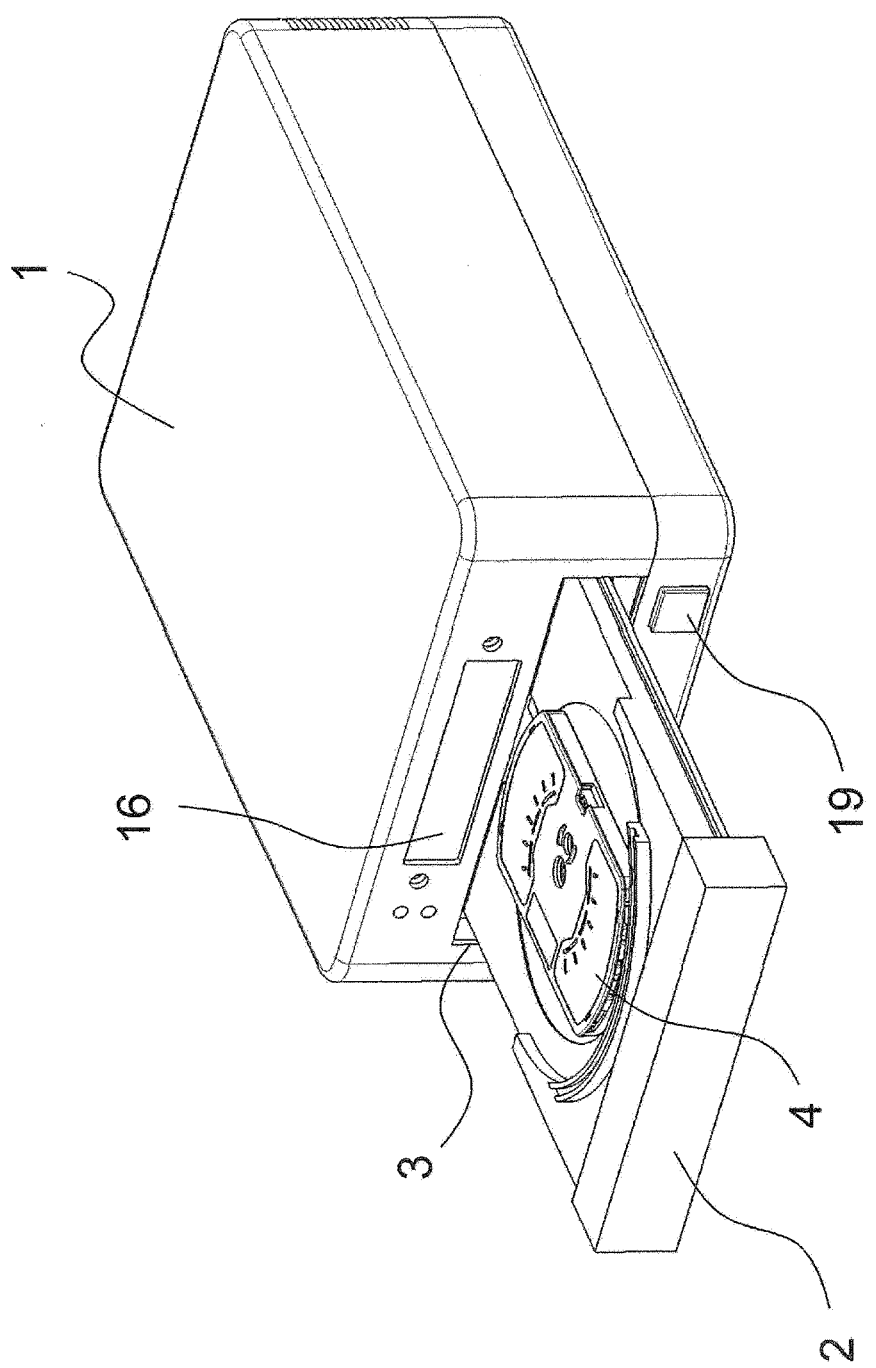
FIG. 4 is an oblique view of the genetic analysis device in an embodiment of the present invention.
Figure 5:
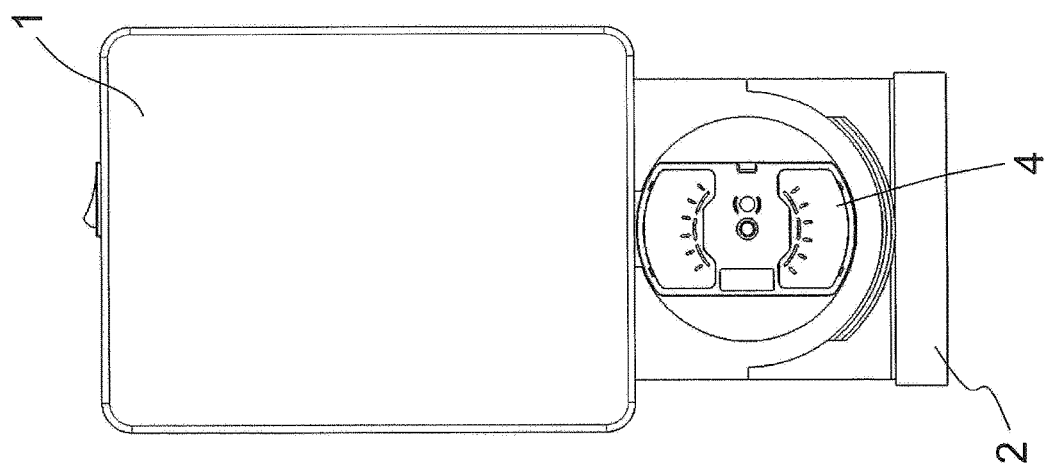
FIG. 5 is a plan view of the genetic analysis device in an embodiment of the present invention.

Specifically, FIG. 1 shows a state in which the analysis receptacle loading tray 2 has been inserted through the opening 3 into the main case 1. FIG. 2 shows a state in which the analysis receptacle loading tray 2 has been pulled out of the main case 1 from the opening 3. As shown in FIGS. 2 to 5, the analysis receptacle loading tray 2 is housed in the main case 1 in a state in which an analysis receptacle 4 (see FIG.

7, etc.) has been placed on its upper face, which allows the analysis receptacle 4 to be conveyed into the main case 1.

Figure 7:
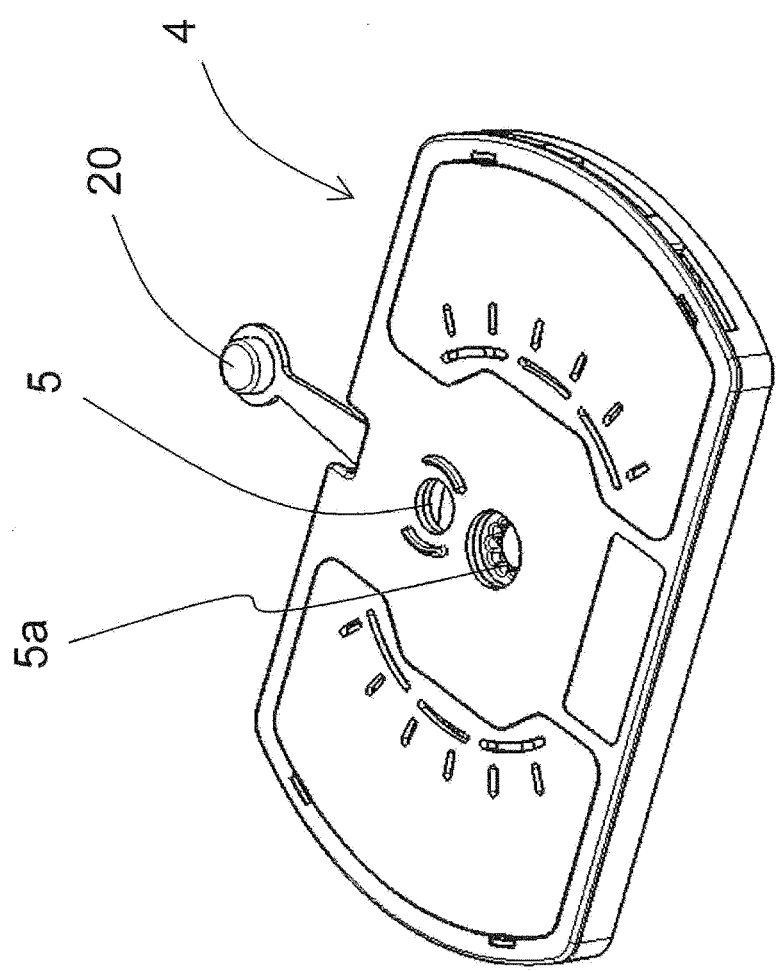
FIG. 7 is an oblique view of an analysis receptacle used in the genetic analysis device in an embodiment of the present invention.
Figure 8:
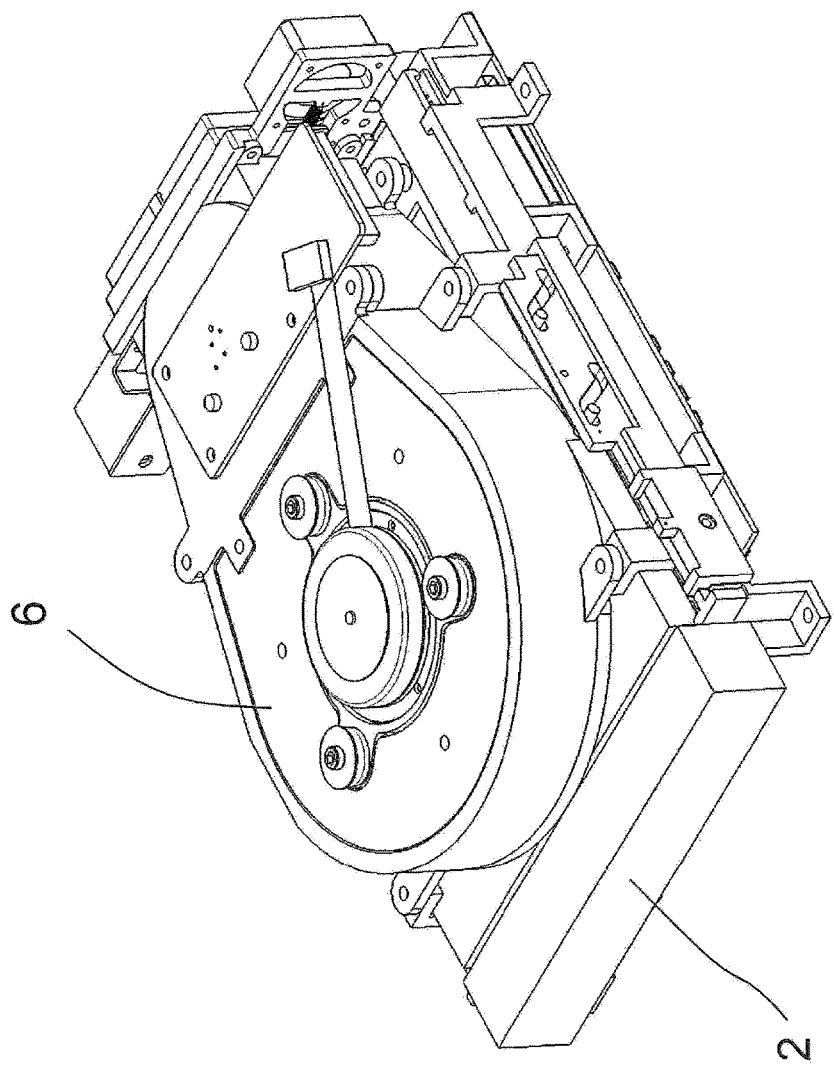
FIG. 8 is an oblique view of the main parts of the genetic analysis device in an embodiment of the present invention.
Figure 9:
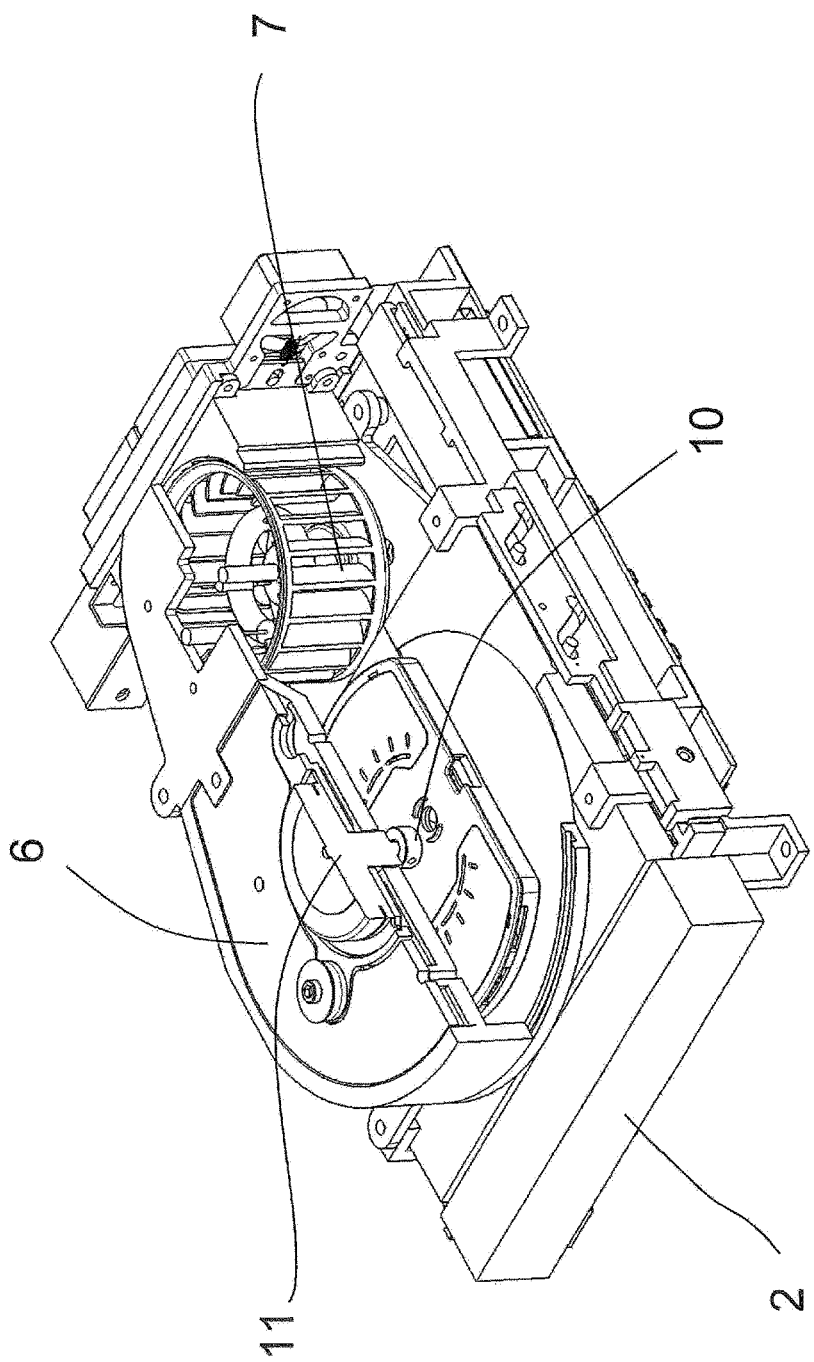
FIG. 9 is a partially cut-away oblique view of the main parts of the genetic analysis device in an embodiment of the present invention.
Figure 10:
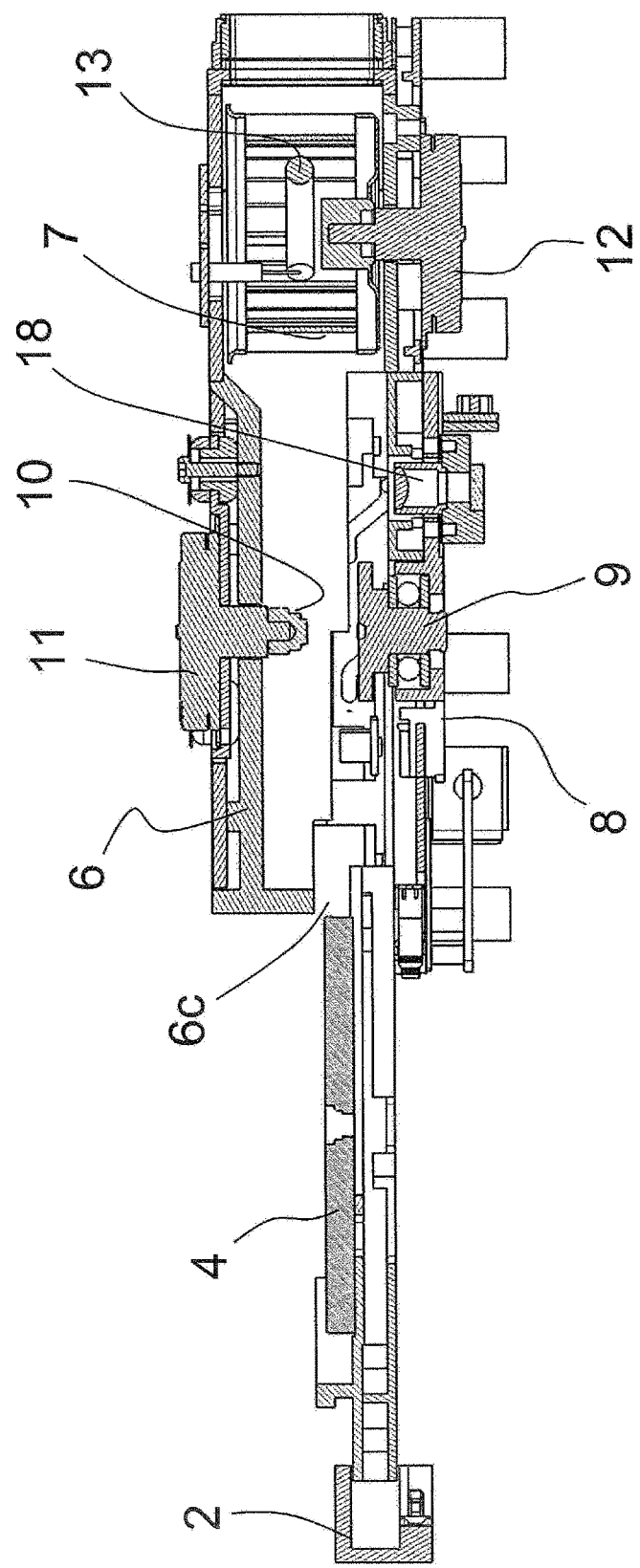
FIG. 10 is a cross section of the main parts of the genetic analysis device in an embodiment of the present invention.
Figure 11:
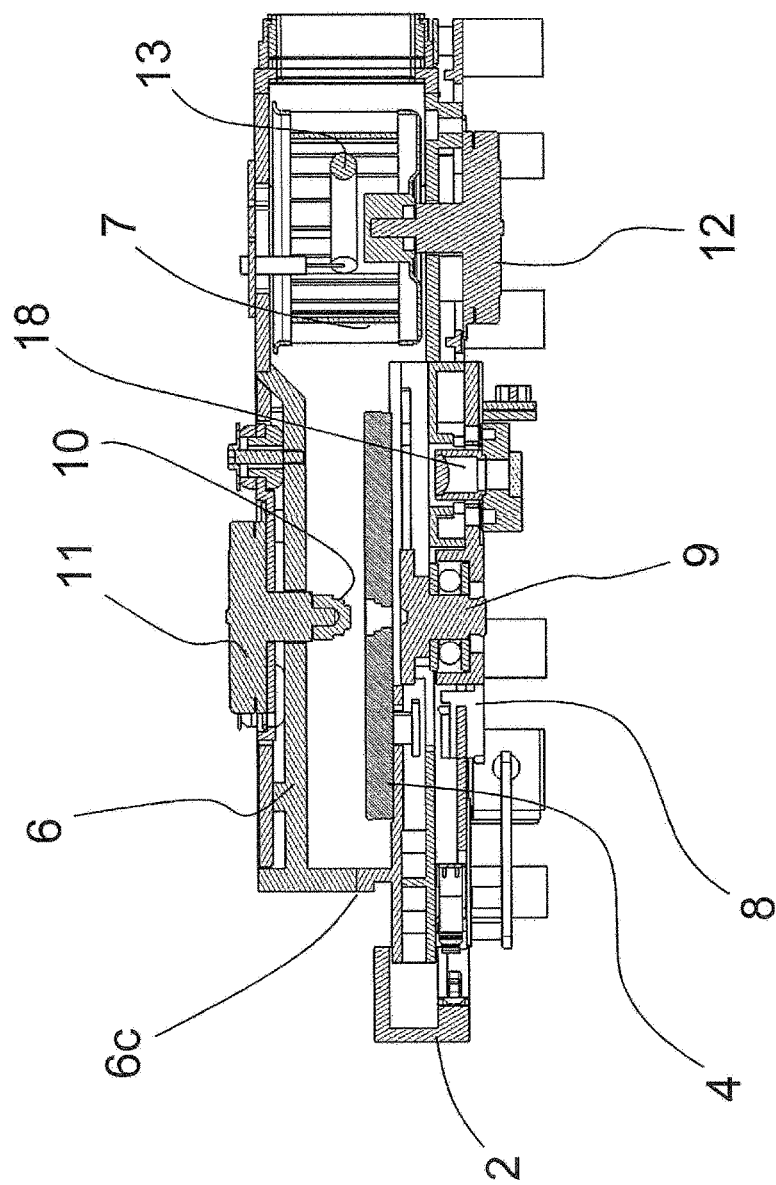
FIG. 11 is a cross section of the main parts of the genetic analysis device in an embodiment of the present invention.
Figure 12:
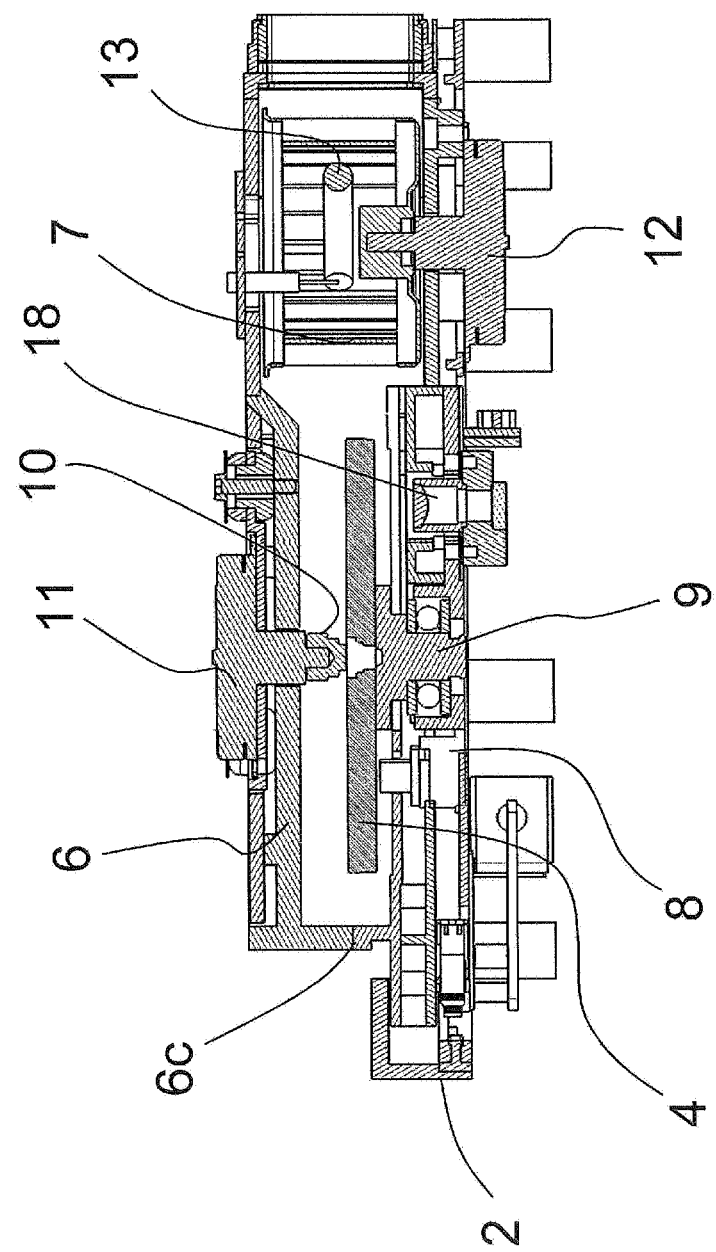
FIG. 12 is a cross section of the main parts of the genetic analysis device in an embodiment of the present invention.

The analysis receptacle 4 is used for the analysis of genes, and a specimen is poured into it through an opening 5 (see FIG. 7).

Next, the opening 5 of the analysis receptacle 4 is covered by a lid 20 (see FIG. 7), and the analysis receptacle 4 is set in this state on the analysis receptacle loading tray 2.

The analysis receptacle 4 is such that the specimen poured in through the opening 5 is branched off at a plurality of places by branching channels, and the specimen and the reagent are reacted in the various parts. Consequently, genes can be analyzed by the reaction situation at the various parts.

The analysis receptacle 4 will be described in detail later on.

The analysis chamber 6 shown in FIGS. 8 to 15 is provided deep inside the opening 3 of the main case 1.

As shown in FIGS. 10 to 13, the analysis receptacle loading tray 2 is inserted into the analysis chamber 6, or pulled out of the analysis chamber 6.

Figure 6:
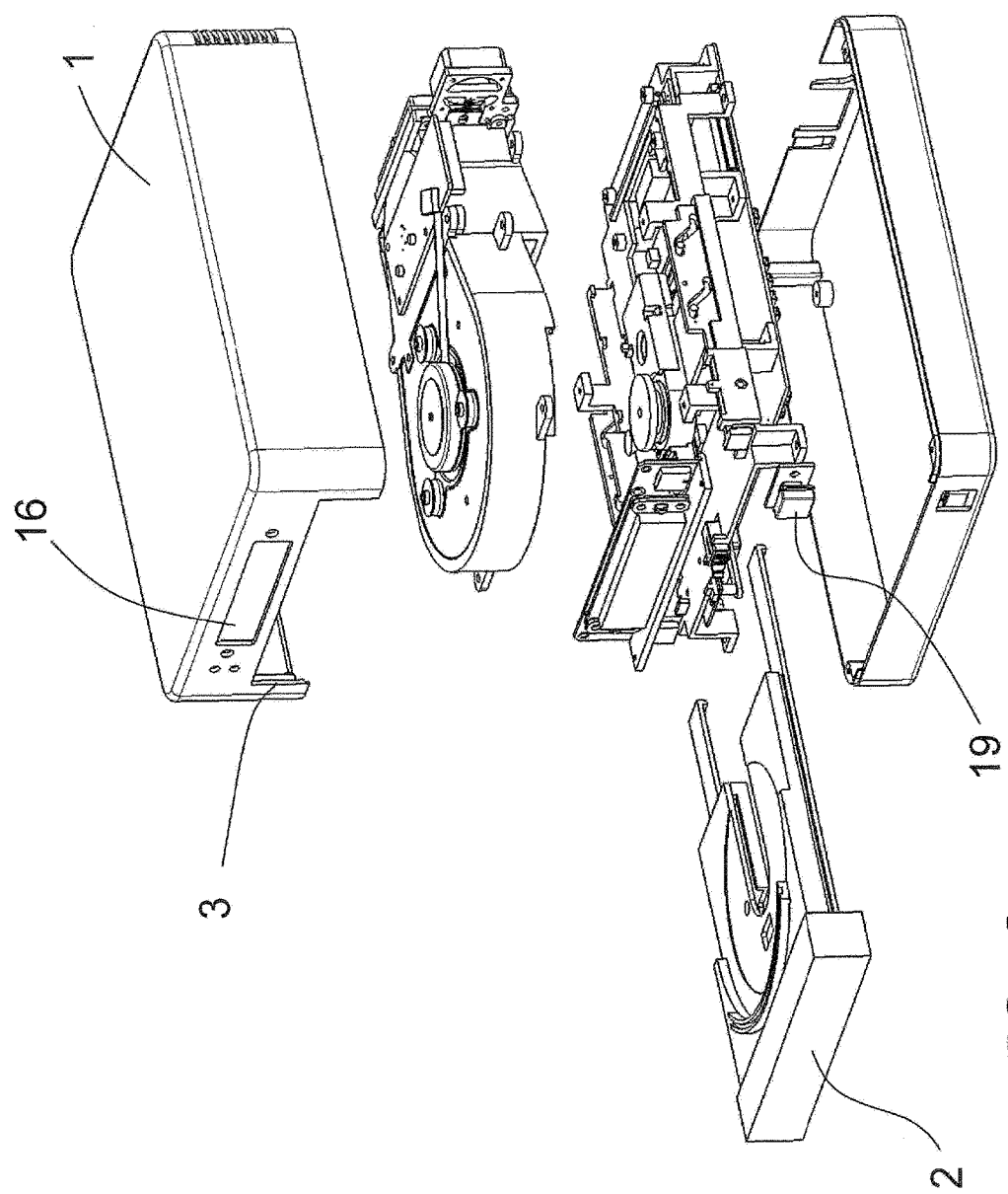
FIG. 6 is an exploded oblique view of the genetic analysis device in an embodiment of the present invention.

More specifically, as shown in FIG. 6, the analysis chamber 6 has a shape in which a small round part 6a that houses a fan 7 and a large round part 6b that houses the analysis receptacle rotary driver 8 shown in FIGS. 10 to 13 are linked via common tangents.

The small round part 6a forms a substantially cylindrical space that is formed around the rotational axis of the fan 7, and has an inside diameter that is slightly larger than the outside diameter of the fan 7.

The large round part 6b forms a substantially cylindrical space that is formed around the rotational axis of the analysis receptacle 4, and has an inside diameter that is slightly larger than the range over which the analysis receptacle 4 rotates.

An analysis receptacle insertion opening 6c is provided to the large round part 6b of the analysis chamber 6. The analysis receptacle loading tray 2 is able to move in and out of the analysis chamber 6 through the analysis receptacle insertion opening 6c.

The analysis receptacle rotary driver 8 is provided to the large round part 6b of the analysis chamber 6.

The analysis receptacle rotary driver 8 has a bearing 9 that rotatably supports the analysis receptacle 4.

As shown in FIGS. 10 to 13, the bearing 9 is raised up when the analysis receptacle loading tray 2 is inserted through the analysis receptacle insertion opening 6c into the analysis chamber 6. As a result, it axially supports a rotary shaft insertion hole 5a of the analysis receptacle 4, so that the analysis receptacle 4 is coupled to a rotary driveshaft 10 provided above and inside the analysis chamber 6.

The rotary driveshaft 10 is also linked to a motor 11. Therefore, in the state in FIG. 13, the analysis receptacle 4 is axially supported in a state of between squeezed from above and below by the rotary driveshaft 10 and the bearing 9, and is rotated by the motor 11.

Meanwhile, the fan 7 is provided to the small round part 6a of the analysis chamber 6.

Figure 15:
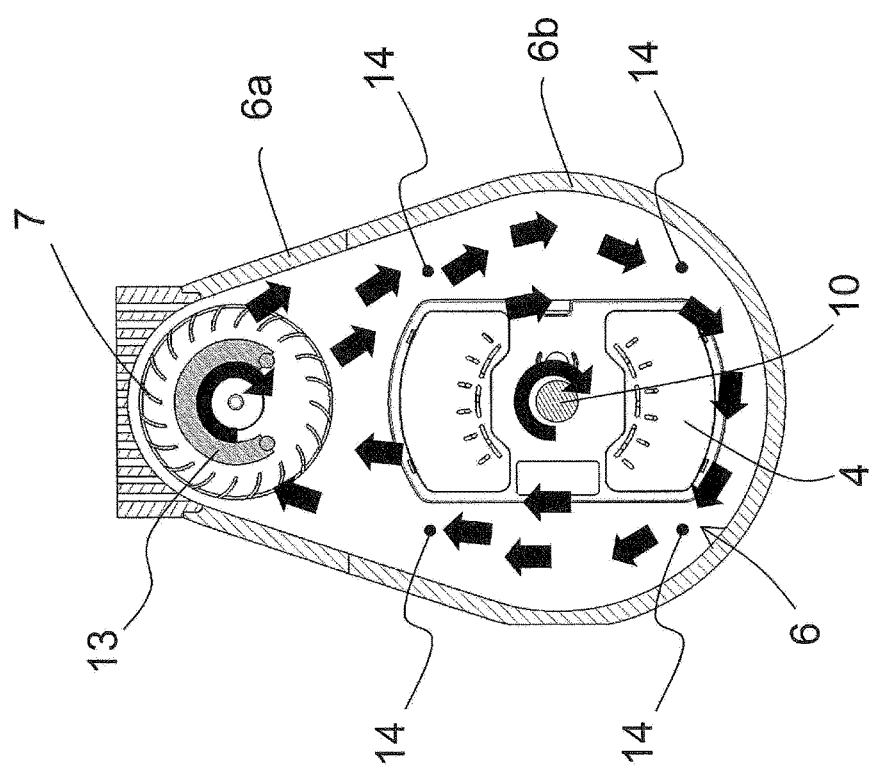
FIG. 15 is a cross section of the main parts of the genetic analysis device in an embodiment of the present invention.

The fan 7 is driven by a motor 12, and as shown in FIG. 15, it forms a clockwise air flow within the analysis chamber 6. A heater 13 is provided in the interior of the fan 7 within the analysis chamber 6. That is, air that has been heated by the heater 13 is sent by the fan 7 in the direction of the large round part 6b of the analysis chamber 6.

Figure 13:
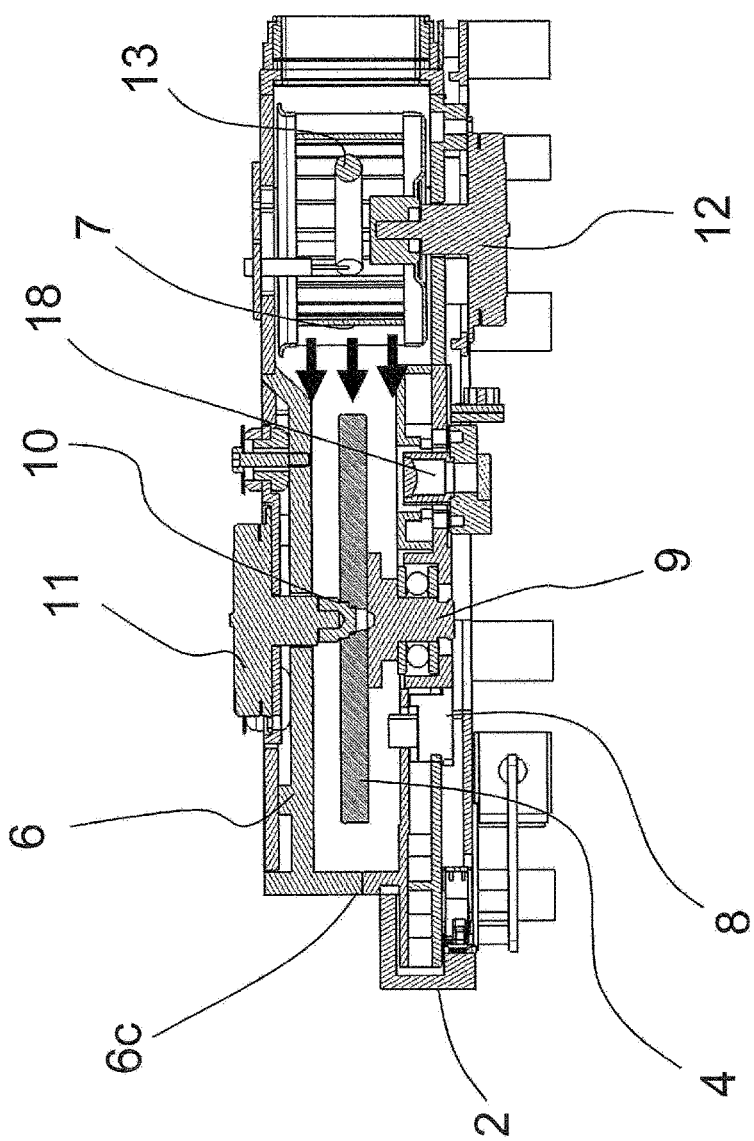
FIG. 13 is a cross section of the main parts of the genetic analysis device in an embodiment of the present invention.
Figure 14:
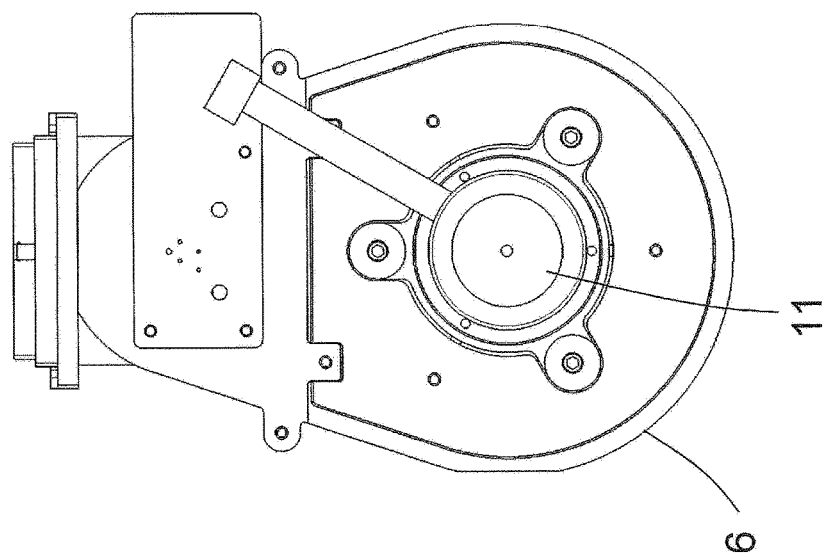
FIG. 14 is a plan view of the main parts of the genetic analysis device in an embodiment of the present invention.

As shown in FIG. 13, the fan 7 is provided to the side of the analysis receptacle 4, and produces an air flow that goes toward the analysis receptacle 4.

As shown in FIG. 13, the fan 7 has a discharge opening that a height equal to the dimension in the height direction in the analysis chamber 6 in which the analysis receptacle 4 is placed. Thus, the air flow produced by the fan 7 produces a substantially uniform air flow over an entire height range equal to the height of the analysis chamber 6.

More specifically, the air flow produced by the fan 7 forms a substantially uniform air flow both above and below the analysis receptacle 4 in the height direction of the analysis chamber 6.

As discussed above, the analysis receptacle 4, which is axially supported in a state of being squeezed from above and below by the rotary driveshaft 10 and the bearing 9, and which is rotated by the motor 11, is disposed in the large round part 6b.

In this embodiment, the direction of air flow formed by the fan 7 in the interior of the analysis chamber 6 is the same as the rotation direction of the analysis receptacle 4 rotated by the motor 11. That is, in the plan view of FIG. 15, the direction of the air flow formed by the fan 7 and the rotation direction of the analysis receptacle 4 are both clockwise.

Therefore, as shown in FIG. 15, the air flow sent out by the fan 7 forms a circulation path that goes from the small round part 6a to the large round part 6b of the analysis chamber 6, goes clockwise around the outer peripheral portion of the rotating analysis receptacle 4, and returns from the large round part 6b to the small round part 6a.

As shown in FIG. 15, four temperature sensors 14 are disposed at 90-degree spacing around the rotary driveshaft 10, at the outer peripheral portion of the rotary driveshaft 10, in the large round part 6b on the circulation path. The four temperature sensors 14 each sense the temperature of the large round part 6b inside the analysis chamber 6.

Figure 16:
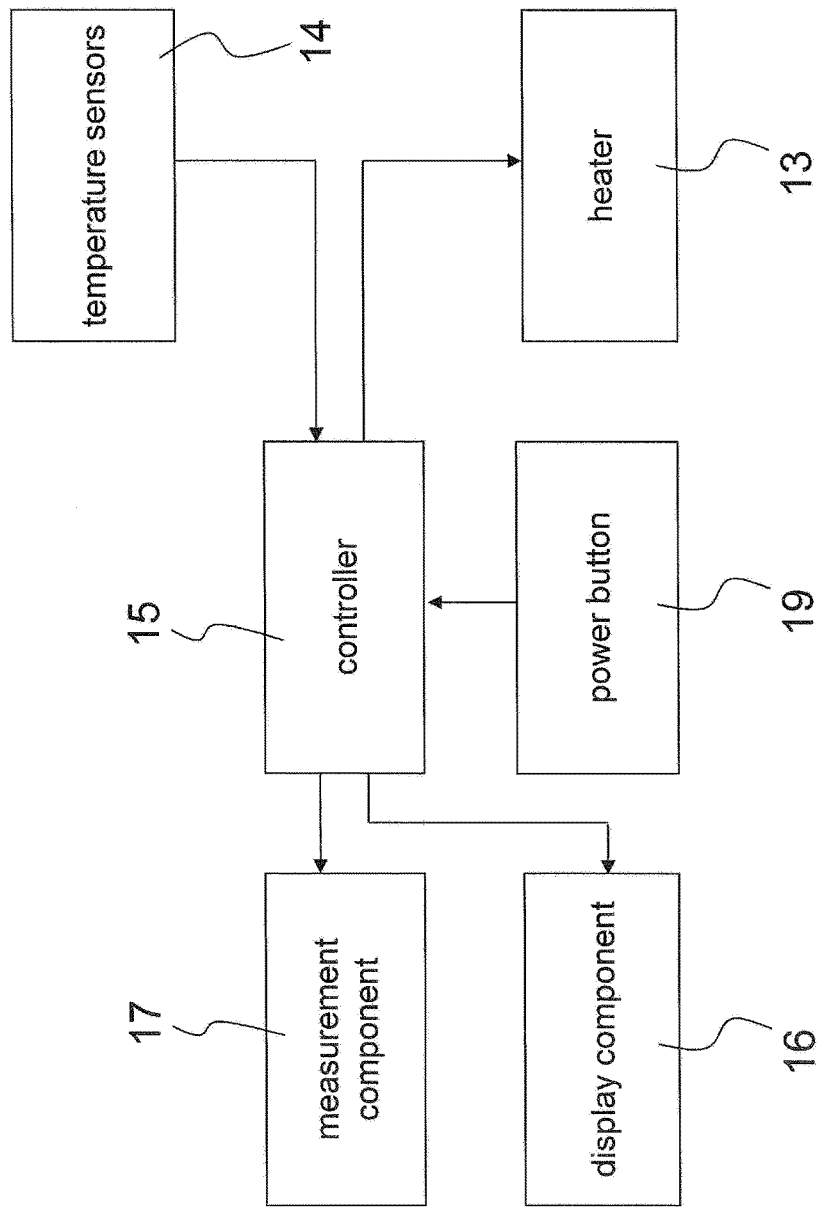
FIG. 16 is a control block diagram of the genetic analysis device in an embodiment of the present invention.

As shown in FIG. 16, the four temperature sensors 14 are connected to a controller 15. The heater 13 is connected to the controller 15.

Consequently, the heater 13 is controlled by the controller 15. As a result, the temperature of the large round part 6b in the analysis chamber 6 is kept at the preset target temperature. Thus, the reaction in the analysis receptacle 4 proceeds stably under a stable analysis environment. This results in better accuracy in gene analysis.

Let us discuss this point in further detail. In this embodiment, as mentioned above, the fan 7 and the heater 13 are provided to the small round part 6a of the analysis chamber 6. Furthermore, in this embodiment the analysis receptacle 4 that is disposed in the large round part 6b of the analysis chamber 6 is rotated by the motor 11.

Figure 17:
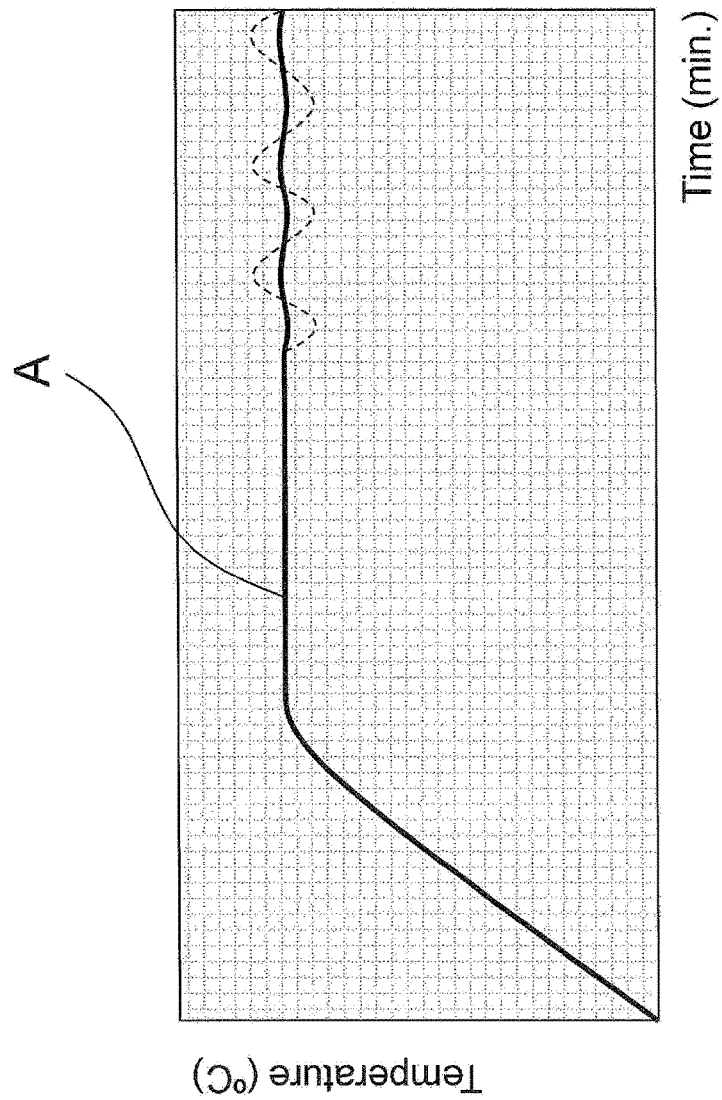
FIG. 17 shows the operation of the genetic analysis device in an embodiment of the present invention.

Therefore, the temperature in the analysis chamber 6 is constant, as indicated by the A line shown in FIG. 17. Thus, the reaction in the analysis receptacle 4 proceeds stably. As a result, gene analysis accuracy can be improved.

In particular, in this embodiment the direction of the air flow formed by the fan 7 is the same as the rotation direction of the analysis receptacle 4 that is rotated by the motor 11.

Therefore, as shown in FIG. 15, the air flow produced by the fan 7 forms a circulation path that goes from the small round part 6a to the large round part 6b of the analysis chamber 6, goes clockwise around the outer peripheral portion of the rotating analysis receptacle 4, and returns from the large round part 6b to the small round part 6a. As a result, the air is stirred and less of it is stagnant. Therefore, the temperature inside the analysis chamber 6 can be kept substantially constant, as indicated by the A line shown in FIG. 17. Thus, the reaction in the analysis receptacle 4 proceeds stably, and as a result gene analysis accuracy can be improved over that in the past.

Furthermore, the rotation direction of the fan 7 is the same as the rotation direction of the analysis receptacle 4 that is rotated by the motor 11 (in this embodiment, clockwise in plan view). Accordingly, there will be no collision of forced air at the portion between the small round part 6a and the large round part 6b of the analysis chamber 6. As a result, less noise will be generated by disturbance of the forced air.

The Y axis in FIG. 17 indicates the temperature of the large round part 6b in the analysis receptacle 4 sensed by the temperature sensors 14. When the analysis receptacle 4 is rotating at a low speed (when first actuated), the temperature of the large round part 6b of the analysis chamber 6 is thought to be low. When the rotational speed of the analysis receptacle 4 reaches its set value, however, the temperature of the large round part 6b of the analysis chamber 6 is thought to stabilize.

As shown in FIG. 1, the display component 16 shown in FIG. 16 is disposed above the opening 3, and displays the drive state, sensing results, etc.

As discussed above, a measurement component 17 reads genes by using an optical sensor 18 (see FIGS. 10 to 13) from under the analysis receptacle 4 that is being rotationally driven.

The measurement component 17 and the display component 16 were already known in the past, so they will not be described in detail here, to avoid over-complicating the description.

As shown in FIG. 1, the power button 19 shown in FIG. 16 is provided under the opening 3.

As discussed above, the genetic analysis device in this embodiment comprises the analysis chamber 6, the fan 7 that is provided inside the analysis chamber 6, the heater 13 that heats air sent from the fan 7 to the analysis receptacle 4, and the analysis receptacle rotary driver 8 that is disposed a specific distance away from the fan 7 in the blowing direction of the fan 7 inside the analysis chamber 6. The rotation direction of the fan 7 is the same as the direction in which the analysis receptacle 4 is rotated by the analysis receptacle rotary driver 8. Therefore, analysis accuracy can be improved over that in the past.

Specifically, in this embodiment, the air heated by the heater 13 is blown by the fan 7 in the direction of the analysis receptacle rotary driver 8 and the analysis receptacle 4 that is rotationally driven by the analysis receptacle rotary driver 8.

As shown in FIG. 15, the direction in which the analysis receptacle 4 is rotated by the analysis receptacle rotary driver 8 is the same as the direction of flow of the air produced by the fan 7.

Consequently, the air is stirred also at the analysis receptacle rotary driver 8 and the analysis receptacle 4 portions. As a result, temperature unevenness can be kept extremely low at the analysis receptacle rotary driver 8 and the analysis receptacle 4. Therefore, analysis accuracy can be improved over that in the past.

Also, since the direction of air flow formed by the fan 7 is the same as the rotation direction of the analysis receptacle rotary driver 8 and the analysis receptacle 4, the air does not collide at the peripheral part of the analysis receptacle 4 (the analysis receptacle rotary driver 8). Therefore, the blowing of air generates less noise.

When genetic analysis with the analysis receptacle 4 is complete, as shown in FIGS. 10 to 13, the analysis receptacle loading tray 2 is pulled out of the main case 1 through the opening 3.

At this point, the bearing 9 of the analysis receptacle rotary driver 8 gradually descends in response to the processing that pulls out the analysis receptacle loading tray 2. In the state in FIG. 11, the analysis receptacle 4 is placed on the analysis receptacle loading tray 2. This allows the analysis receptacle loading tray 2 to be pulled out smoothly from the opening 3 of the main case 1 and the analysis receptacle insertion opening 6c of the analysis chamber 6.

The basic configuration in this embodiment was described above, and the various constituent elements will now be described in further detail.

Figure 18:
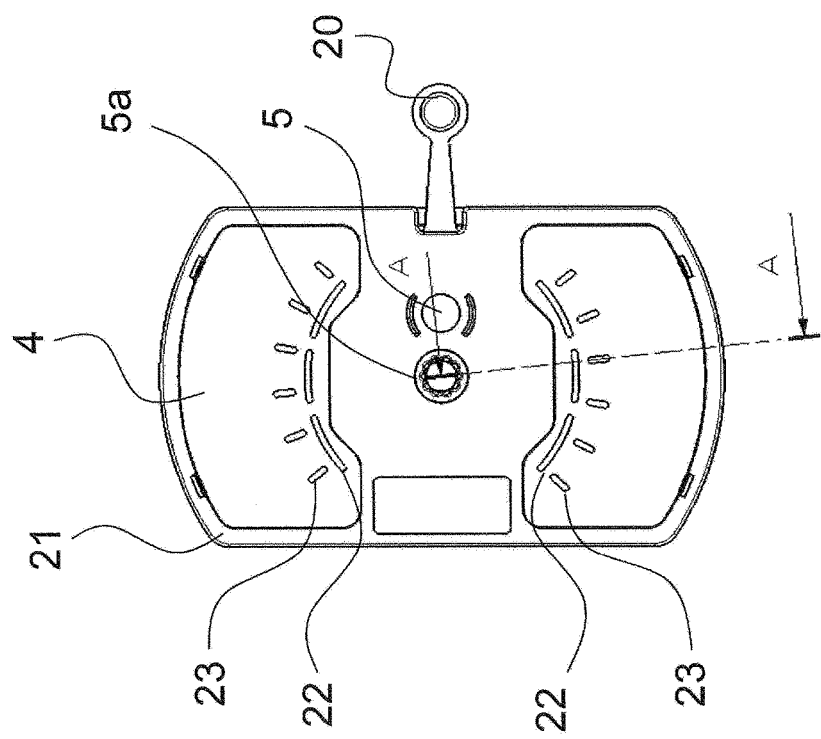
FIG. 18 is a plan view of the main parts of the analysis receptacle in an embodiment of the present invention.

FIG. 18 is a top view of the analysis receptacle 4.

The analysis receptacle 4 is used for the genetic analysis of a specimen, for example, and as shown in FIG. 18, has a main case 21, the rotary shaft insertion hole 5a that is provided in the center of the main case 21 and into which a rotary shaft is inserted, the opening 5 into which the specimen is poured, the lid 20 for sealing off the opening 5, a first air intake opening 22 that is provided around a circle centered on the rotary shaft inside the rotary shaft insertion hole 5a, and a second air intake opening 23 that is provided in the radial direction centered on the rotary shaft.

Figure 19:
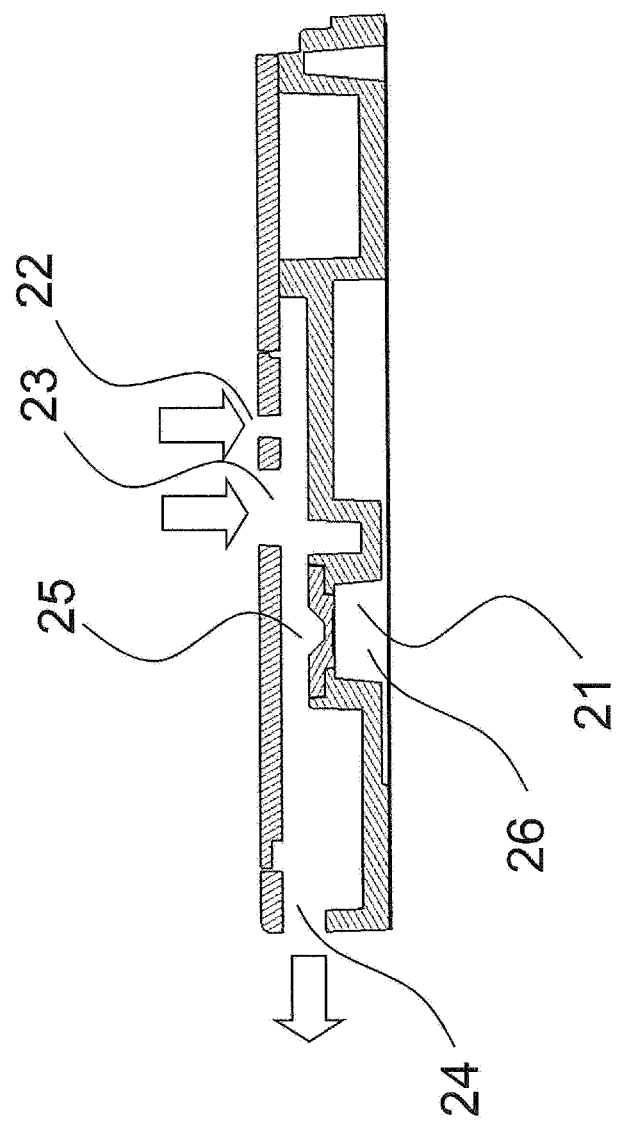
FIG. 19 is a cross section of the main parts of the analysis receptacle in an embodiment of the present invention.

FIG. 19 is a lateral cross section along the A line in FIG. 18.

An air discharge opening 24 is provided to the side face of the analysis receptacle 4.

The air discharge opening 24 communicates with the first air intake opening 22 and the second air intake opening 23 via a channel 25 inside the main case 21 of the analysis receptacle 4.

Figures 20A, 20B:
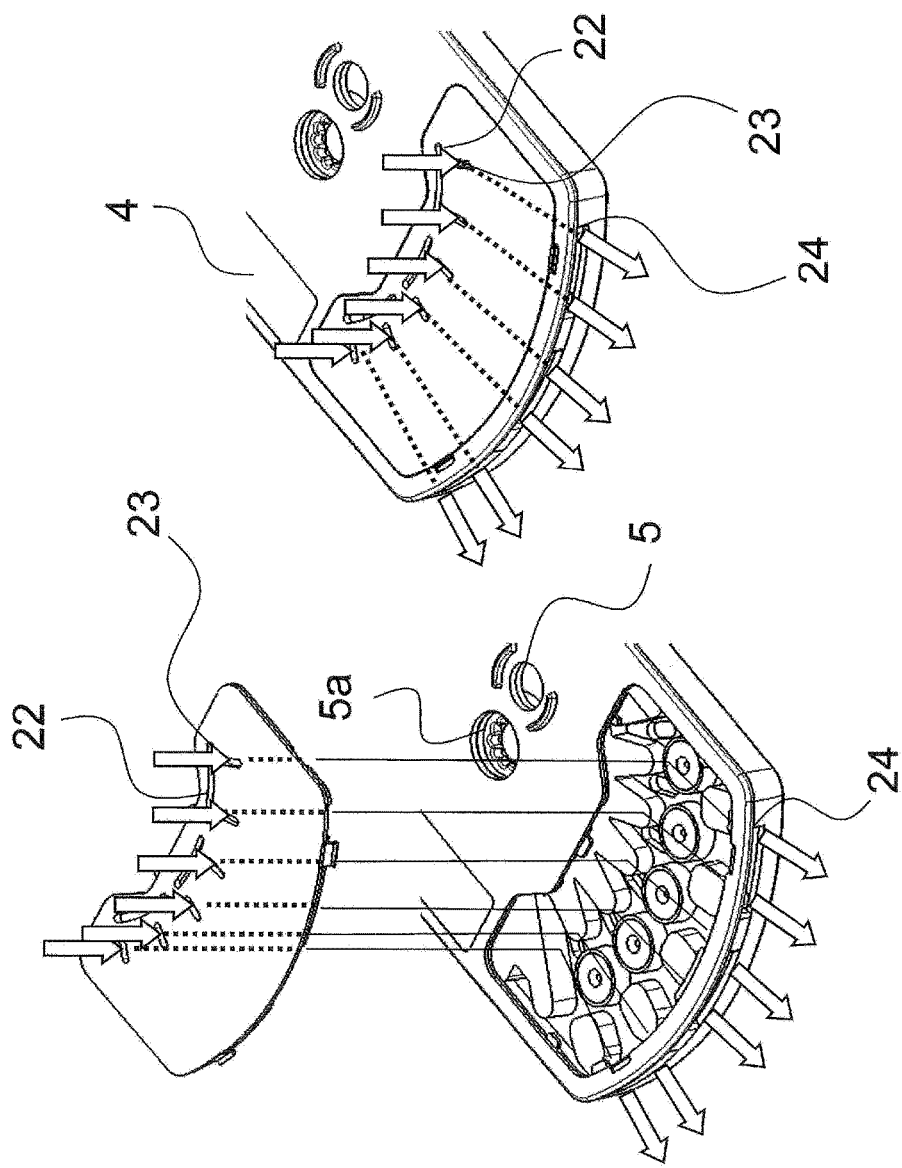
FIGS. 20A and 20B are oblique views of the main parts of the analysis receptacle in an embodiment of the present invention.

Consequently, when the analysis receptacle 4 is mounted to the analysis device and rotationally driven, as shown in FIGS. 20A and 20B, the air that has flowed in through the first air intake opening 22 and the second air intake opening 23 escapes from the air discharge opening 24 through the channel 25.

As shown in FIGS. 19 and 21, a reaction component 26 is provided along the channel 25 inside the main case 21.

As shown in FIG. 19, the first air intake opening 22 and the second air intake opening 23 are provided on the inner peripheral side of the reaction component 26. The air discharge opening 24 is provided on the outer peripheral side of the reaction component 26.

With the above configuration, when the main case 21 is rotated by the rotary driveshaft 10, heat air is drawn in under the negative pressure generated at the rotary driveshaft 10 portion. Next, the heated air is drawn into the main case 21 from the first air intake opening 22 and the second air intake opening 23. After this the heated air passes the outer periphery of the reaction component 26, and is then discharged from the air discharge opening 24 to outside the main case 21.

That is, in this embodiment, the temperature-controlled heated air passes directly through the outer periphery of the reaction component 26. Accordingly, the temperature of the reaction component 26 can be kept at the set temperature, and as a result the analysis accuracy can be improved.

Also, the opening surface area of the air discharge opening 24 is larger than the opening surface areas of the first air intake opening 22 and the second air intake opening 23. This improves the air intake and discharge efficiency, so the reaction component 26 can be kept at the set temperature.

Next, the reaction component 26 will be described in detail.

FIG. 21 is a top see-through view of the analysis receptacle 4.

The reaction component 26 is provided around a circle centered on the rotary shaft inside the main case 21 of the analysis receptacle 4.

The reaction component 26 has a metering component 27 that meters out specific quantities of the specimen, a plurality of measurement chambers 28, channels 29, a sealing members 29a, stirring chambers 30, and channels 31.

The measurement chambers 28 are provided around the outer periphery of the metering component 27, and allow the reagent to come in and react with the specimen.

The channels 29 are connected to the metering component 27 and to the measurement chambers 28.

The sealing members 29a seal of these channels 29 under a specific temperature, and open up the channels 29 once a specific length of time has passed since this specific temperature is exceeded.

The stirring chambers 30 are provided around the outer periphery of the measurement chambers 28, and stir the reagent and specimen that enter the measurement chambers 28.

The channels 31 are connected to the measurement chambers 28 and the stirring chambers 30.

As shown in FIG. 21, the shape of the main case 21 as seen from above, that is, the contour of the lateral cross sectional shape, has first regions 32a and 32b with a relatively long distance from the rotational axis center, and second regions 33a and 33b with a relatively short distance from the rotational axis center. The contour of the lateral cross sectional shape is in point symmetry with the rotational axis center.

More specifically, the first regions 32a and 32b are formed at positions that are farther than the second regions 33a and 33b from the rotational axis center. Specifically, as shown in FIGS. 18, 21, etc., the contour of the analysis receptacle 4 is not formed in a circular shape whose center is the rotational axis in plan view, but instead is made up of the first regions 32a and 32b that form the exterior of mutually opposing arc shapes, and the second regions 33a and 33b that form the exterior of the straight lines that are perpendicular to these arcs.

In this embodiment, because of the above configuration, when the main case 21 is rotated by the rotary driveshaft 10, the warm air from the fan 7 is blown directly onto the surface of the main case 21 of the rotating analysis receptacle 4. In this state, the main case 21 becomes non-disk-shaped, and in the second regions 33a and 33b, which are at a shorter distance from the rotational axis center, air circulation occurs on the upper and lower sides of the analysis receptacle 4, which stirs the air. As a result, temperature unevenness can be kept to a minimum at the upper face and lower face of the analysis receptacle 4. Thus, temperature of the reaction component 26 of the analysis receptacle 4 can be stably maintained near the target temperature, and this improves analysis accuracy.

The reaction component 26 is provided around a circle that is parallel to the outer peripheral faces of the first regions 32a and 32b. The reaction component 26 is provided at a position that is farther away from the rotational axis center than the distance in the radial direction to the second regions 33a and 33b.

Thus providing the reaction component 26 to the first regions 32a and 32b that are farther away from the rotational axis center than the second regions allows the distance of the reaction component 26 from the rotational axis center to be relatively long. Thus, the centrifugal force exerted on the reaction component 26 can be increased. As a result, the reaction in the reaction component 26 is promoted, and analysis efficiency can be enhanced.

Returning to FIG. 21, we will now describe a channel confirmation component 34.

The channel confirmation component 34 has a first holder 35 and a second holder 36 that are disposed at a specific spacing toward the outer peripheral direction of the rotary shaft hole, a wax channel 37 that connects the first and second holders 35 and 36, wax 38 that seals the wax channel 37, and a seal breakage detector 39 that is housed in the first holder 35.

The configuration here is such that the time when the seal breakage detector 39 housed in the first holder 35 moves to the second holder 36 due to the melting of the wax 38 is later than the time when the specimens housed in the metering component 27 move to the measurement chambers 28 due to the melting of the sealing members 29a.

In a more specific configuration, the melting temperature of the wax 38 in the wax channel 37 that connects the first and second holders 35 and 36 is higher than the melting temperature of the sealing members 29a.

In a second configuration, the cross sectional area of the wax channel 37 that connects the first and second holders 35 and 36 is larger than the cross sectional area of the channels that connect the metering component 27 and the measurement chambers 28.

Consequently, the amount of wax 38 in the wax channel 37 is greater than the amount of the sealing members 29a in the channels 29 that link the measurement chambers 28 to the metering component 27. Thus, since melting takes time, the time when the seal breakage detector 39 housed in the first holder 35 moves to the second holder 36 due to the melting of the wax 38 is later than the time when the specimens housed in the metering component 27 move to the measurement chambers 28 due to the melting of the sealing members 29a.

As a result, whether or not the specimens in the measurement chambers can be analyzed can be determined by confirming whether or not the seal breakage detector 39 has flowed into the second holder 36. Thus, checking for the seal breakage detector 39 in the second holder 36 eliminates excess measurement waiting time, and the analysis can be carried out more quickly.

Next, the rotary shaft insertion hole 5a will be described.

FIG. 22A is a top view of the analysis receptacle 4, and FIG. 22B is a detail view of the A portion around the rotary shaft insertion hole 5a.

The contour of the lateral cross sectional shape of the rotary shaft insertion hole 5a is disposed at regular intervals. A plurality of convex components 40 that stick out in the outer peripheral direction of a circle centered on the rotational axis, concave components 41 that are recessed in the inner peripheral direction between the convex components 40, and continuous curved parts 42 that link the convex components 40 and the concave components 41 are provided around the rotary shaft insertion hole 5a.

The configuration of the rotary driveshaft 10 is shown in FIG. 23 and FIGS. 24A to 24C.

Figure 23:
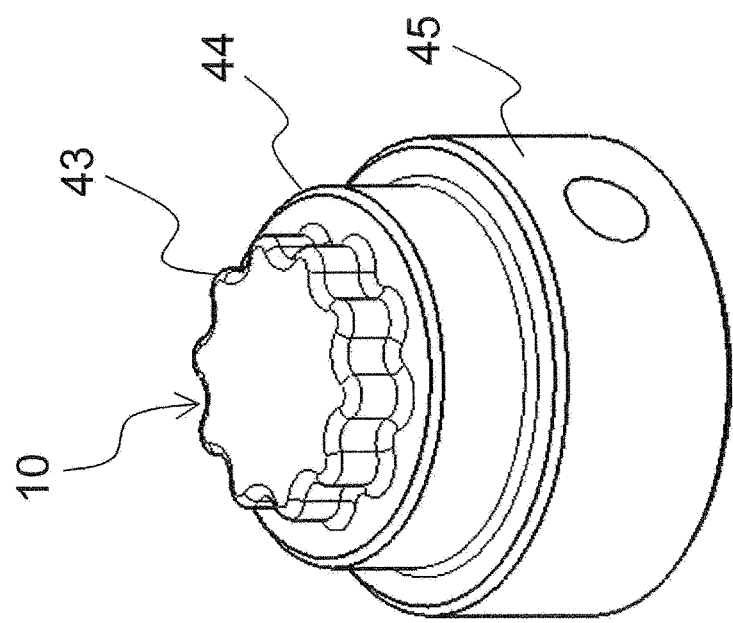
FIG. 23 is an oblique view of the main parts of the genetic analysis device in an embodiment of the present invention.
Figure 24A:
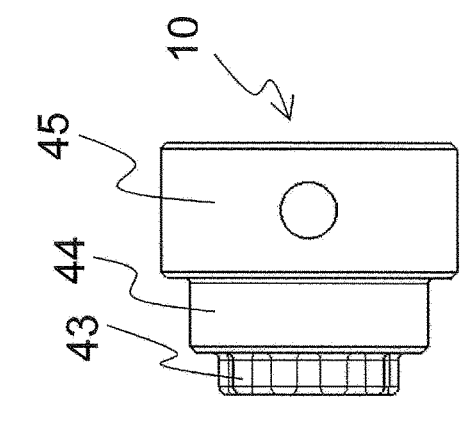
FIGS. 24A to 24C are a plan view, a side view, and a cross section of the main parts of the genetic analysis device in an embodiment of the present invention.

FIG. 23 is an oblique view of the rotary driveshaft 10. FIG. 24A is a top view of the rotary driveshaft 10, FIG. 24B is a side view, and FIG. 24C is a vertical cross section.

Figure 24B:
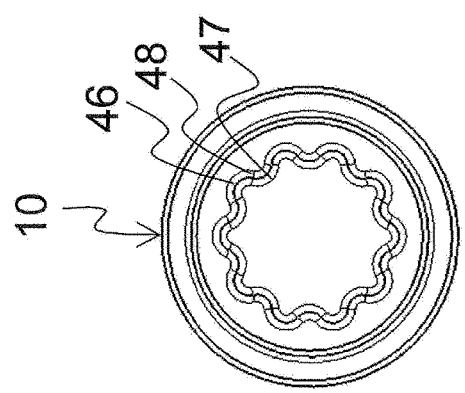
Figure 24C:
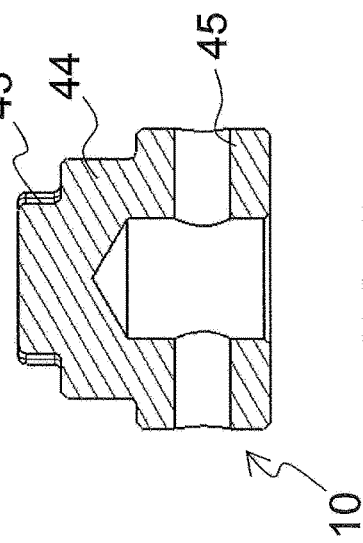

As shown in FIG. 23 and FIGS. 24B and 24C, the rotary driveshaft 10 has a three-stage configuration in which an insertion component 43, an abutting component 44, and a bottom component 45 are provided in that order, starting from the top.

As shown in FIG. 24A, the contour of the lateral cross sectional shape of the insertion component 43 is disposed at regular intervals. A plurality of convex components 46 that stick out in the outer peripheral direction of a circle centered on the rotational axis, concave components 47 that are recessed in the inner peripheral direction between the adjacent convex components 46, and continuous curved parts 48 that link the convex components 46 and the concave components 47 are provided around the rotary shaft insertion hole 5a.

Figure 25A:
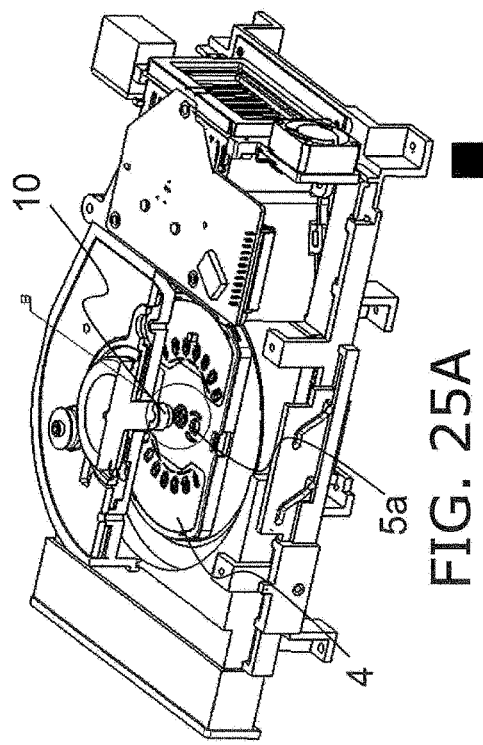
Figure 25B:
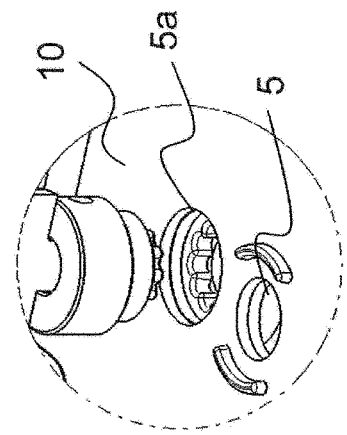
FIGS. 25B and 25D are detail views of the B and C portions in FIGS. 25A and 25C.
Figure 25C:
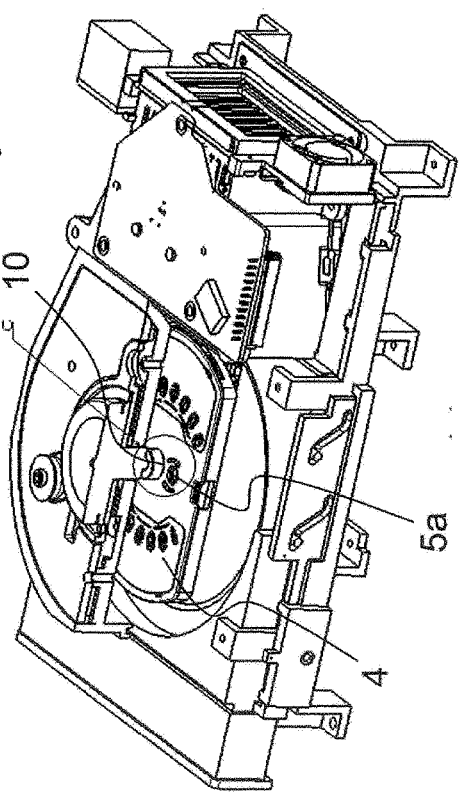
Figure 25D:
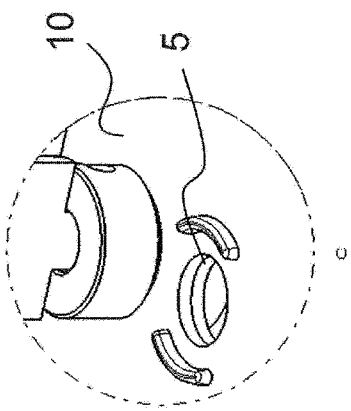

FIGS. 25A and 25B show the state when the analysis receptacle 4 has been mounted to the analysis device.

FIG. 25A shows the state before the rotary driveshaft 10 is inserted into the rotary shaft insertion hole 5a. In this embodiment, the rotary driveshaft 10 is inserted into the rotary shaft insertion hole 5a when the analysis receptacle 4 rises up.

When the rotary driveshaft 10 has been inserted into the rotary shaft insertion hole 5a, this results in a neutral state in which the rotary driveshaft 10 rotates freely. At this point, the curved parts 42 of the contour of the lateral cross sectional shape of the rotary shaft insertion hole 5a come into contact with the curved parts 48 of the lateral cross sectional shape on the rotary driveshaft 10 side, and the concave components and convex components engage while sliding over the curved surfaces of the curved parts 42 and 48. More specifically, the rotary driveshaft 10 (in the neutral state) rotates a tiny distance in the rotation direction while being inserted into the rotary shaft insertion hole 5a of the analysis receptacle 4.

Consequently, the curved parts 42 of the contour of the lateral cross sectional shape of the rotary shaft insertion hole 5a and the curved parts 48 of the lateral cross sectional shape on the rotary driveshaft 10 side are in contact with each other while the concave components and convex components engage while sliding over the curved surfaces of the curved parts 42 and 48. Thus, the rotary driveshaft 10 can be inserted into the rotary shaft insertion hole 5a, and operation is facilitated in the mounting of the analysis receptacle 4.

Furthermore, the analysis receptacle 4 in this embodiment is such that the rotation operation during analysis is accompanied by sudden rotation and sudden braking in order to stir the specimen. Here again, since the rotary driveshaft 10 and the rotary shaft insertion hole 5a are securely engaged by the convex and concave components, there is no slippage of the rotary driveshaft 10 in the rotation direction. As a result, analysis reliability can be improved.

Next, the insertion of the analysis receptacle 4 into the analysis device will be described through reference to FIGS. 26A to 26D.

As shown in FIG. 26A, the analysis receptacle insertion opening 6c is provided to the large round part 6b of the analysis chamber 6. The analysis receptacle loading tray 2 is able to move in and out of the analysis chamber 6 through the analysis receptacle insertion opening 6c.

Also, the analysis receptacle rotary driver 8 is provided to the large round part 6b of the analysis chamber 6. The analysis receptacle rotary driver 8 has the bearing 9 that axially and rotatably supports the analysis receptacle 4.

As shown in FIGS. 26A to 26D, the bearing 9 is lifted upward when the analysis receptacle loading tray 2 is inserted through the analysis receptacle insertion opening 6c into the analysis chamber 6. As a result, the bearing 9 axially supports the rotary shaft insertion hole 5a of the analysis receptacle 4, which allows the analysis receptacle 4 to be linked to the rotary driveshaft 10 provided at the top in the analysis chamber 6.

The rotary driveshaft 10 is linked to the motor 11. Therefore, in the state in FIG. 26D, the analysis receptacle 4 is axially supported in a state of being sandwiched from above and below by the bearing 9 and the rotary driveshaft 10, and is rotated by the motor 11.

The analysis device in this embodiment comprises a bearing block that is provided at the bottom of the analysis chamber 6 and serves as the bottom face of the analysis chamber 6 including the bearing 9, and a drive block that is provided at the top in a state in which the analysis receptacle loading tray 2 is housed inside the main case, and that serves as the top face of the analysis chamber 6 including the motor 11 and the rotary driveshaft 10.

The bearing block and the drive block move toward the analysis receptacle loading tray 2 side in a state in which the analysis receptacle loading tray 2 is housed inside the main case 21. This improves analysis accuracy.

Specifically, in this embodiment, the analysis chamber 6 in the analysis device in which the analysis receptacle loading tray 2 is located is clamped by the bearing block and the drive block, and becomes a closed space that surrounds the analysis receptacle loading tray 2. Thus, the air in the analysis chamber 6 is blocked off from the air outside the analysis chamber 6, which makes it easier to keep the temperature inside the analysis chamber 6 at the target temperature, and as a result the analysis accuracy can be improved.

In this embodiment, an example was described in which the bearing block was provided on the lower side of the analysis chamber 6, and the drive block on the upper side of the analysis chamber 6, but the present invention is not limited to or by this. For instance, the bearing block may be provided on the upper side of the analysis chamber 6, and the drive block on the lower side of the analysis chamber 6.

The analysis process in this embodiment will now be described through reference to FIGS. 27A to 27F.

FIG. 27A shows the temperature state in each process within the analysis chamber 6. FIG. 27B shows the rotational speed of the analysis receptacle 4 in each process.

First, in the preparation step, as shown in FIG. 27C, a specimen solution is poured in through the opening 5 of the analysis receptacle 4. The analysis receptacle 4 is then placed on the analysis receptacle loading tray 2 and inserted into the analysis device as discussed above.

Next, in the metering step, as shown in FIG. 27D, the analysis receptacle 4 that has been inserted into the analysis device is rotationally accelerated to 3500 rpm, and is rotated for 10 seconds. In this state, the specimen solution that has come in through the opening 5 of the analysis receptacle 4 is evenly distributed by the metering component 27 to all areas under the large centrifugal force produced by the high-speed rotation.

Then, in the wax dissolution step, first, as shown in FIG. 27A, after the metering step, the inside of the analysis chamber 6 is heated to 60° C. (the target temperature) by the heater 13. In this step, since the specimen solution does not need to be subjected to a large centrifugal force, the rotational speed of the analysis receptacle 4 is lowered from 3500 rpm to 100 rpm and held there, as shown in FIG. 27B.

In this state, as shown in FIGS. 27D and 27E, the sealing members 29a in the channels 29 that link the metering component 27 and the measurement chambers 28 in the analysis receptacle 4 melt at a temperature of 60° C. Consequently, the melting of the sealing members 29a causes the specimens housed in the metering component 27 to move into the measurement chambers 28.

Whether or not the specimens housed in the metering component 27 have moved to the measurement chambers 28 can be reliably confirmed as follows. The seal breakage detector 39 of the channel confirmation component 34 shown in FIG. 21 confirms that there has been movement from the first holder 35 to the second holder 36.

Next, in the stirring step, as shown in FIG. 27B, the rotational speed of the analysis receptacle 4 is held at 3000 rpm for 5 seconds and at 500 rpm for 5 seconds, and this cycle is repeated. Consequently, as shown in FIG. 27E, the reagents and specimen solutions in the measurement chambers 28 are subjected to different centrifugal forces according to the changes in the rotational speed. Accordingly, the specimen solutions are stirred while going through the channels 31 that link the respective measurement chambers 28 and the stirring chambers 30.

Next, in the measurement step, as shown in FIG. 27A, the temperature inside the analysis chamber 6 is held at 60° C., and as shown in FIG. 27B, in this state the rotational speed of the analysis receptacle 4 is held at 240 rpm. This state is maintained for 60 minutes, and as shown in FIG. 27F, measurement is performed by observing the fluorescent light in each of the measurement chambers.

In this embodiment, as discussed above, the rotational speed of the analysis receptacle 4 is varied in the metering step, the wax dissolution step, the stirring step, and the measurement step.

Consequently, the feed, metering, and stirring of the specimen solution within the analysis receptacle 4 can be effectively carried out in the various steps.

Figure 28:
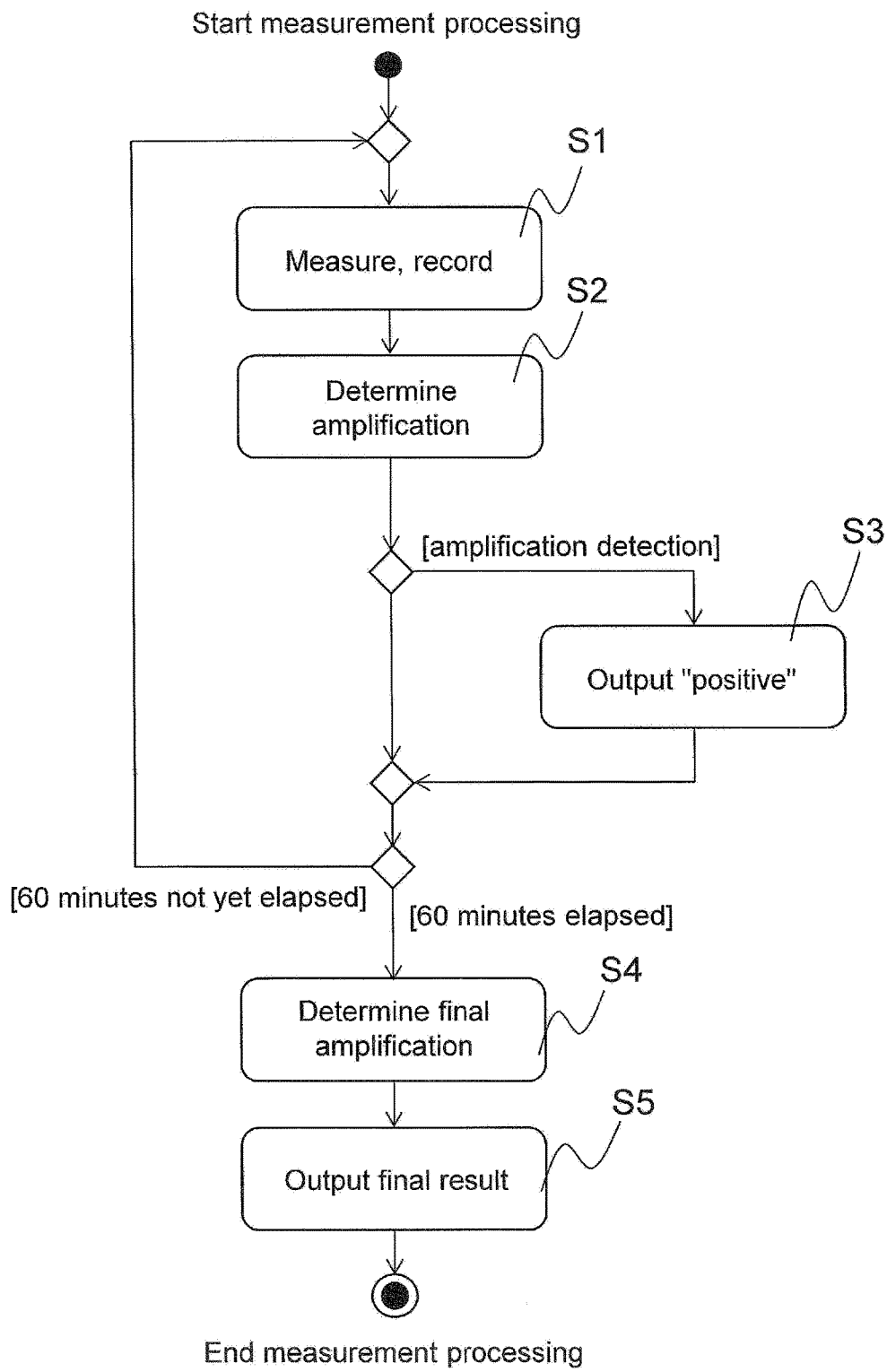
FIG. 28 is a flowchart of the genetic analysis device in an embodiment of the present invention.

FIG. 28 is a flowchart of the measurement step.

The basic flow, as discussed above, is that after the rotational speed of the analysis receptacle 4 has been held at 240 rpm for 60 minutes, whether or not a particular gene is present is determined from whether or not the absolute value of the intensity of the amount of fluorescent light in each measurement chamber is greater than a specific value, as a final amplification determination step (S4). The final result is displayed on the display component 16.

With this determination method, in the past it was necessary to observe the intensity of the fluorescent light after a specific amount of time had elapsed, so the analysis took a long time. A method for solving this problem will now be described.

First, a gene amplifier is used on the specimen, and this specimen is reacted with a reagent that contains a substance in which a fluorescent reagent is bonded to a primer that undergoes a specific reaction with a particular gene sequence, and it is determined whether or not the particular gene is present. Then, after specific gene amplification of the specimen has begun, whether or not the particular gene is present is determined from whether or not a differential value for the intensity of fluorescent light of the fluorescent reagent that undergoes a specific reaction with the particular gene is above a specific threshold. This method shortens the analysis time.

Figure 29:
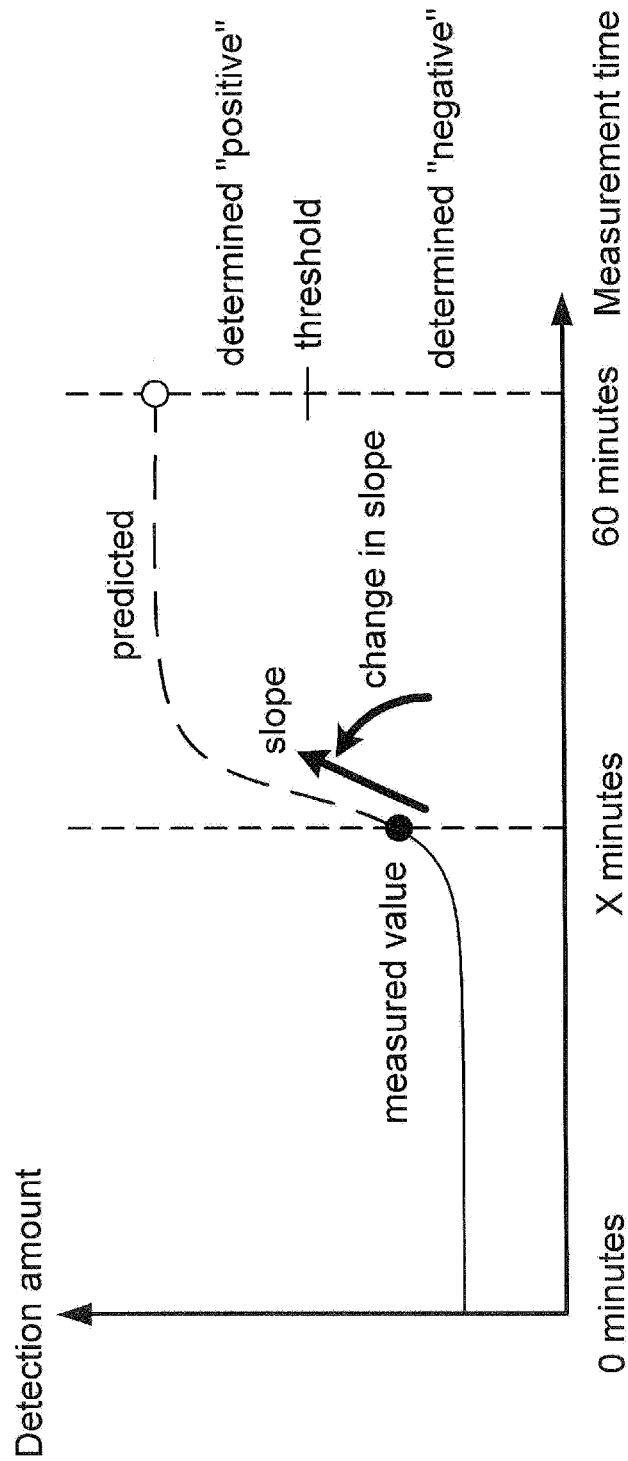
FIG. 29 is a graph of the relation between the detected amount and the measured time of the genetic analysis device in an embodiment of the present invention.

The details of this will be described in further detail through reference to FIGS. 28 and 29.

In the measurement step, if the result is positive, that is, if the particular gene is present, after a specific amount of time has elapsed, then the change amount by which that gene is amplified is used as a specific range. In the measurement step, this change amount is successively observed.

More specifically, the differential value for the intensity of fluorescent light is measured, and whether or not the change amount by which the gene is amplified is within the specific range is confirmed by monitoring the values of first-stage differentiation and second-stage differentiation of the differential value (S1 and S2 in FIG. 28).

If this change amount is within the specific range, the result is deemed positive, and the output is displayed on the display component 16 (S3 in FIG. 28).

Specifically, in this embodiment, the change amount of the intensity of fluorescent light of the fluorescent reagent that undergoes a specific reaction with a particular gene is successively monitored as a differential value, and this differential value is used to determine whether or not the gene is present.

Consequently, whether or not the gene is present can be immediately determined from the change amount of the gene, so the analysis can be completed in less time.

Furthermore, this change amount is determined by determining that the differential value for the intensity of fluorescent light is greater than a specific value when the intensity of fluorescent light, that is, the amount of the gene, is over a specific threshold. This allows more accurate determination to be performed.

Next, the temperature control in the measurement step will be described as an example of the fuzzy control pertaining to this embodiment.

As shown in FIG. 27A, as discussed above, in the measurement step it is necessary to set the temperature inside the analysis chamber 6 to 60° C. In general, the temperature inside a chamber where measurement is performed will be lower than 60° C., so the inside of the analysis chamber 6 has to be heated to raise the temperature to 60° C.

Figure 30:
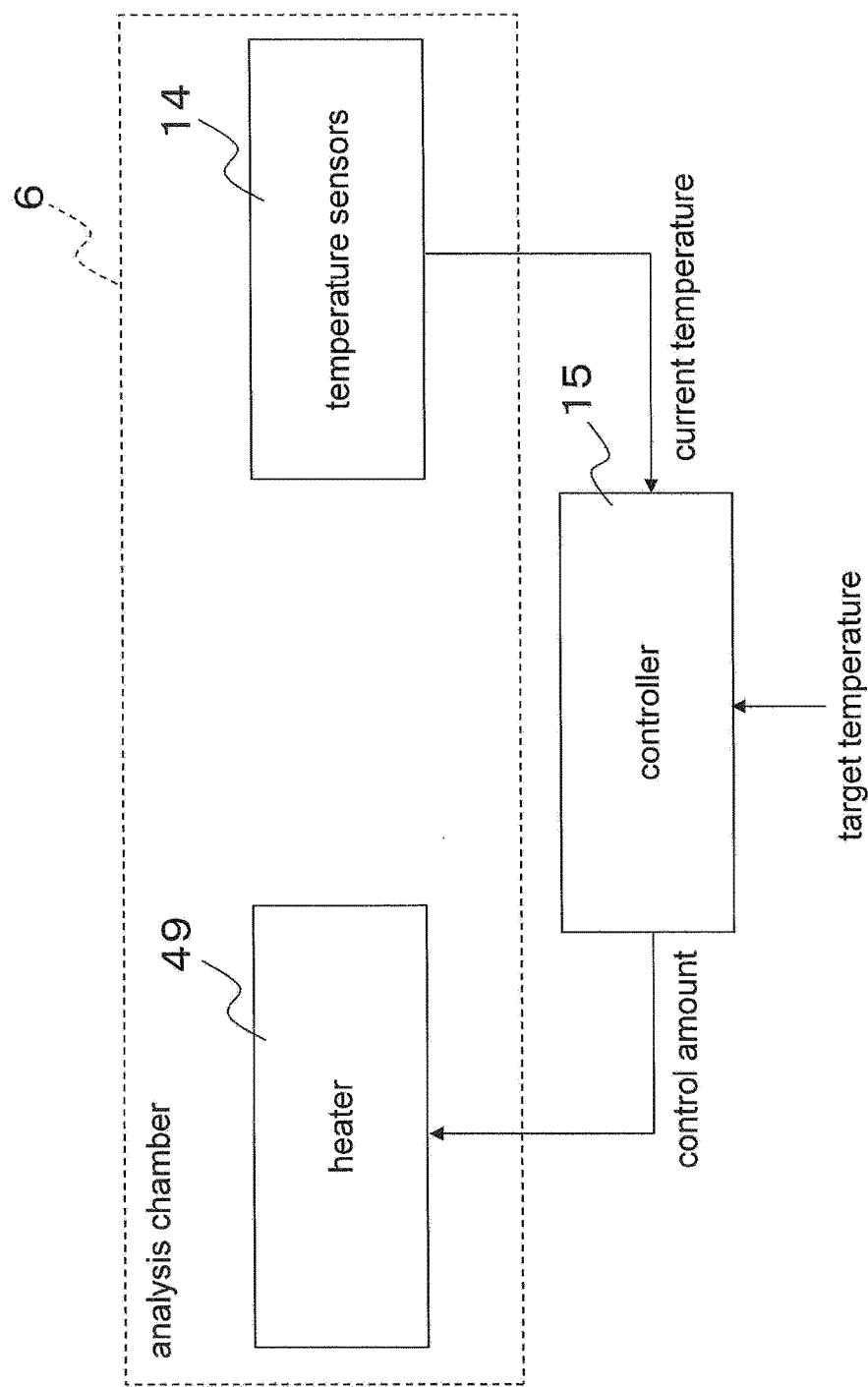
FIG. 30 is a control block diagram of the temperature control device in an embodiment of the present invention.

FIG. 30 is a control block diagram of the temperature control device pertaining to this embodiment.

This temperature control device comprises the analysis chamber 6, the temperature sensors 14 (temperature measurement components) that measure the temperature inside the analysis chamber 6, a heater 49 provided inside the analysis chamber 6, and the controller 15 that monitors the temperature sensors 14 and subjects the heater 49 to feedback control so that the temperature inside the analysis chamber 6 will become the target temperature.

The controller 15 performs fuzzy control for target temperature setting. More specifically, the controller 15 produces fuzzy sets for the outputs of deviation and deviation rate, and performs temperature control on the basis of these fuzzy sets.

The term deviation here is the differential value obtained by subtracting the current temperature from the target temperature, and is obtained by calculating the difference between the target temperature 60° C. and the current temperature read from the temperature sensors 14 once every second. That is, if the deviation is a positive value, it means that the current temperature is lower than the target temperature, but if the deviation is a negative value, it means that the current temperature is higher than the target temperature.

The deviation rate is the differential value obtained by subtracting the deviation one second ago from the current deviation.

For example, if the deviation rate is a negative value, and the deviation is a positive value, it means that the current temperature is approaching the target temperature from a state of being lower than the target temperature. On the other hand, if the deviation rate is a negative value, and the deviation is a negative value, it means that the current temperature has gone over the target temperature and is moving to a higher temperature.

If the deviation rate is a positive value, and the deviation is a positive value, it means that the current temperature has dropped lower from a state of already being lower than the target temperature, and is moving away from the target temperature. On the other hand, if the deviation rate is a positive value, and the deviation is a negative value, it means that the current temperature is decreasing from a state of being over the target temperature, and is now approaching the target temperature.

Figure 31:
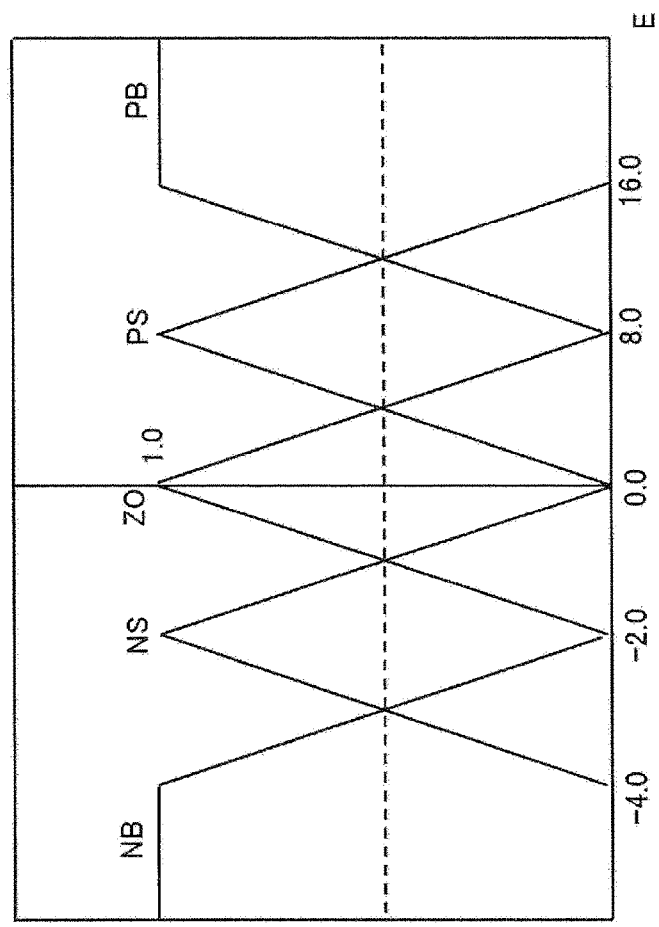
FIG. 31 shows fuzzy sets in the temperature control method in an embodiment of the present invention.

FIG. 31 shows fuzzy sets of deviation.

There are five fuzzy sets of deviation.

More specifically, these are ZO (near zero, a triangle whose vertex is 0 and whose bottom side is from 8.0 to −2.0), PS (positive small, a triangle whose vertex is 8.0 and whose bottom side is from 16.0 to 0.0), PB (positive big, a stepped shape with a sloped side that rises to the right from 8.0 to 16.0 and that is flat from 16.0 and beyond), NS (negative small, a triangle whose vertex is −2.0 and whose bottom side is from 0.0 to −4.0), and NB (negative big, a stepped shape with a sloped side that rises to the left from −2.0 to 4.0 and that is flat from −4.0 and beyond).

Figure 32:
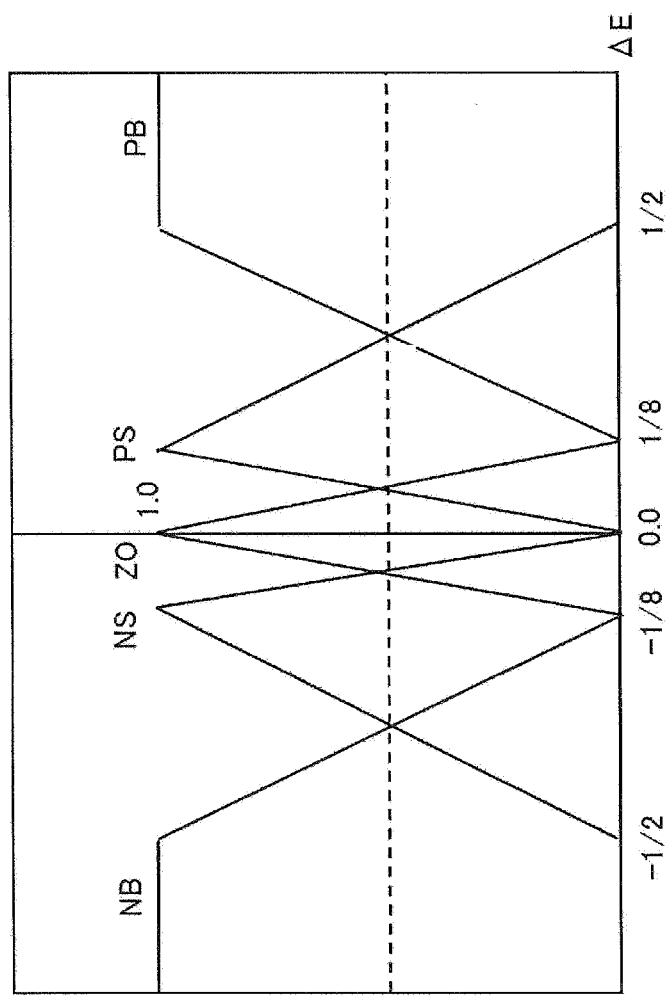
FIG. 32 shows fuzzy sets in the temperature control method in an embodiment of the present invention.

FIG. 32 shows the fuzzy sets for deviation rate.

There are five fuzzy sets for deviation rate. More specifically, these are ZO (near zero, a triangle whose vertex is 0 and whose bottom side is from ⅛ to −⅛), PS (positive small, a triangle whose vertex is ⅛ and whose bottom side is from ½ to 0.0), PB (positive big, a stepped shape with a sloped side that rises to the right from ⅛ to ½ and that is flat from ½ and beyond), NS (negative small, a triangle whose vertex is −⅛ and whose bottom side is from 0.0 to −½), and NB (negative big, a stepped shape with a sloped side that rises to the left from −⅛ to −½ and that is flat from −½ and beyond).

Figure 33:
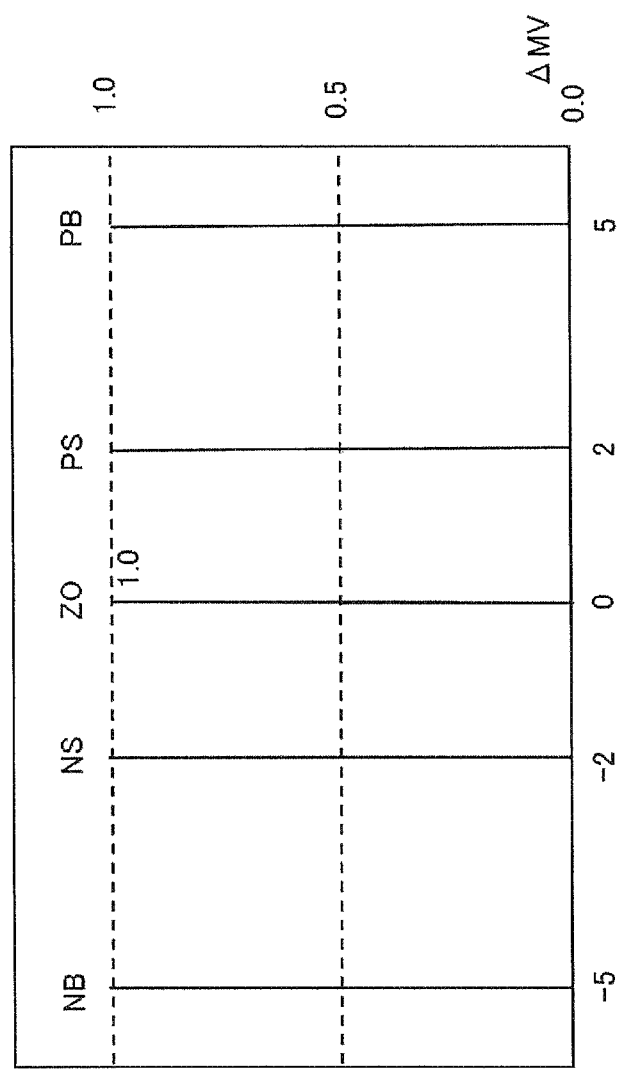
FIG. 33 shows fuzzy sets in the temperature control method in an embodiment of the present invention.

FIG. 33 shows the fuzzy sets for output.

There are five fuzzy sets for output. To facilitate calculation, these were formed as simple pulses of ZO=0, PS=2, PB=5, NS=−2, and NB=−5.

FIG. 34 shows fuzzy rules in which the above three types of fuzzy set are used.

In the table of fuzzy rules in FIG. 34, the first row in the lateral direction shows fuzzy sets for deviation. The first column on the left shows the fuzzy sets for deviation rate. The fuzzy set for output is indicated by the elements in the table shown at the intersections of the fuzzy sets for deviation and the fuzzy sets for deviation rate.

The current temperature can be controlled to be the target temperature by performing control according to these fuzzy rules.

Figure 35:
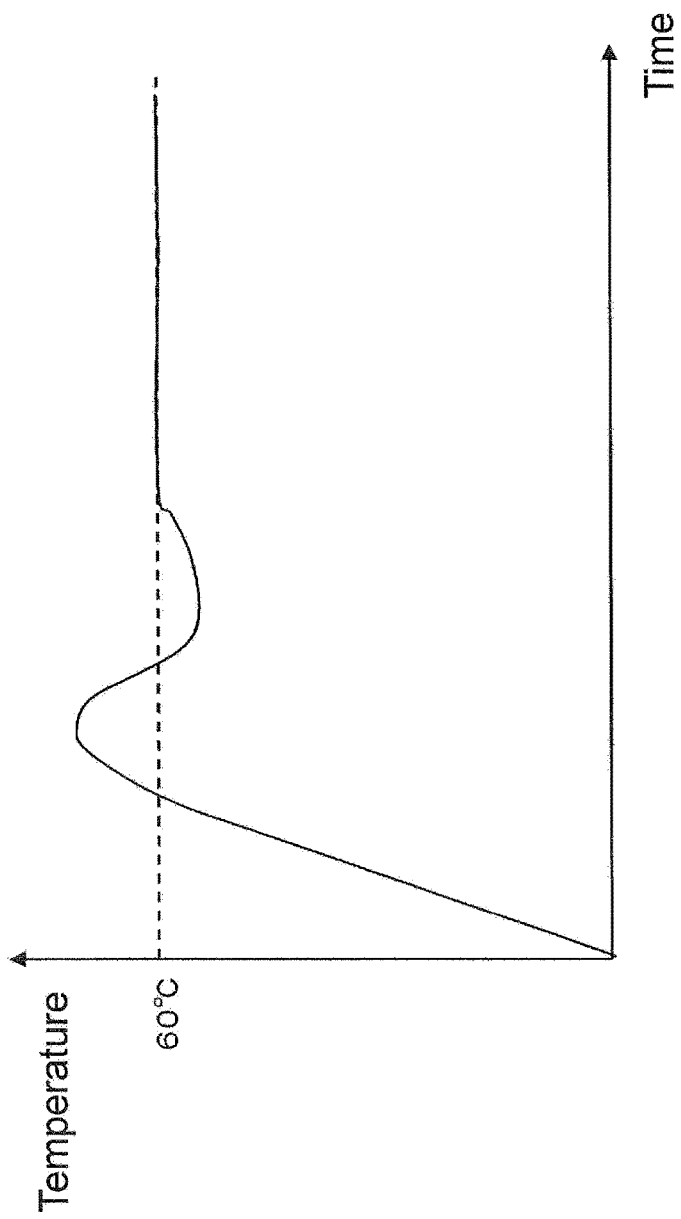
FIG. 35 shows the temperature response characteristics for the temperature control method in an embodiment of the present invention.
Figure 36:
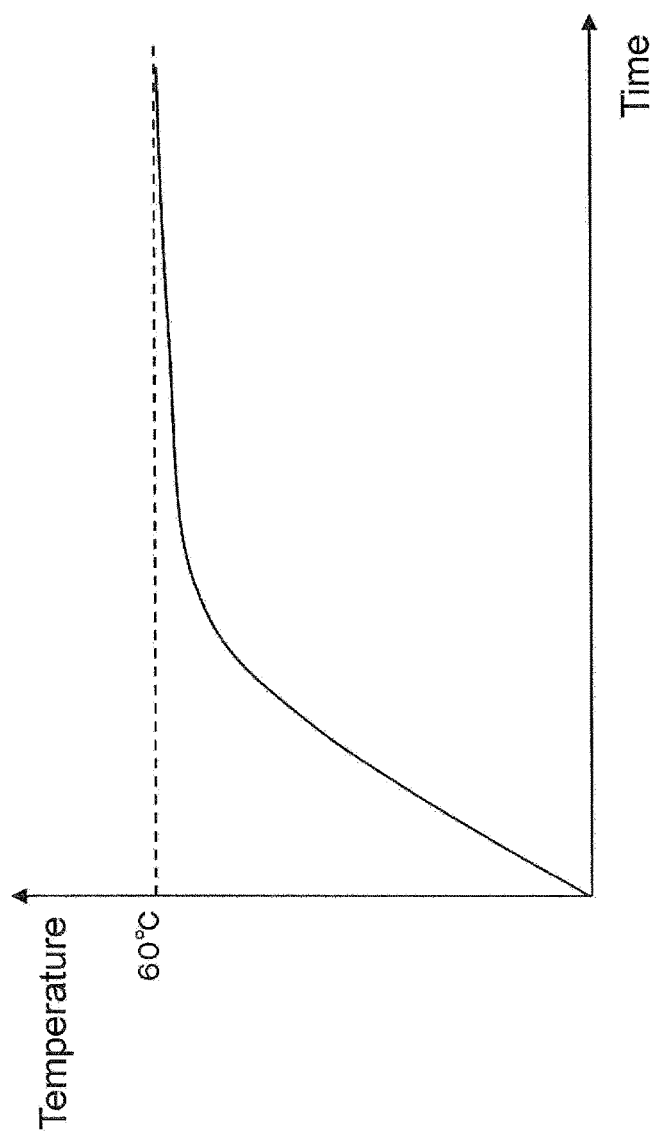
FIG. 36 shows the temperature response characteristics for the temperature control method in an embodiment of the present invention.

However, depending on the temperature of the ambient environment of the temperature control device, the temperature may be overshot as shown in FIG. 35, or it may take a long time to reach the target temperature as shown in FIG. 36, so there may be situations when responsiveness is unstable.

In particular, today's genetic analysis devices need for the target temperature to be reached quickly and stably, without overshooting the temperature.

The reagent used for gene analysis here will only react properly near the target temperature. Therefore, below the target temperature, it is necessary to reach the target temperature and eliminate the excessively high temperature state quickly, and it is also necessary not to go over the target temperature (that is, without overshooting the temperature), so there is a need for stable responsiveness regardless of the temperature of the ambient environment of the temperature control device.

In view of this, in this embodiment the temperature response characteristics are monitored, and the fuzzy sets for deviation are updated according to these response characteristics.

More specifically, the time axis response characteristics for the current temperature are monitored, and it is determined whether or not the overshoot value has exceeded 0.5° C. (specific value).

Figure 37:
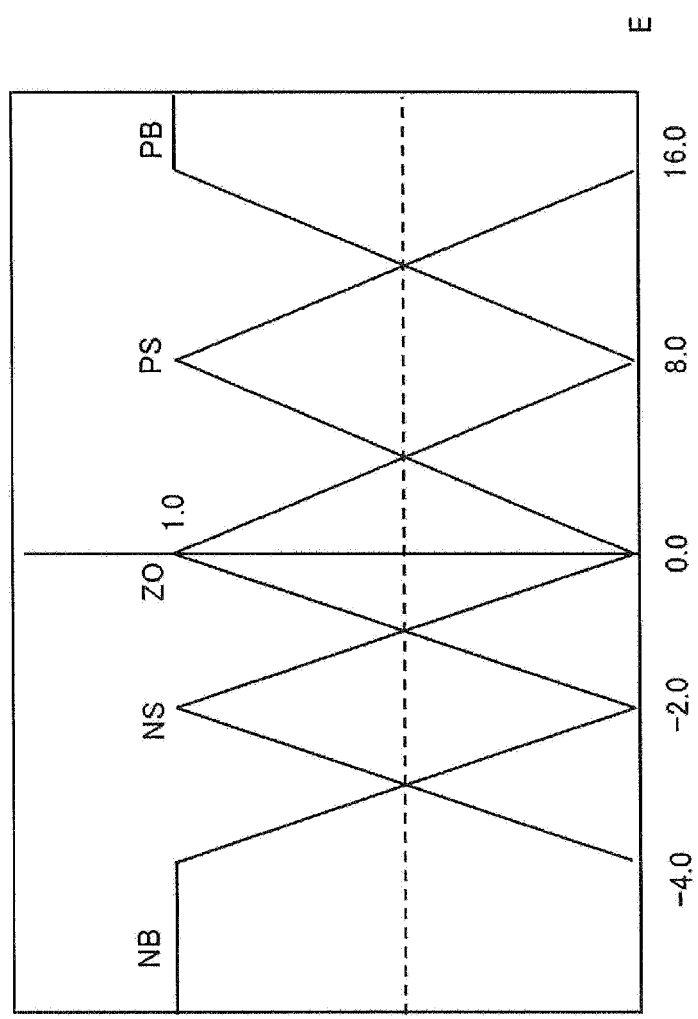
FIG. 37 shows fuzzy sets in the temperature control method in an embodiment of the present invention.

If the overshoot value here has exceeded the specific value of 0.5° C., as shown in FIG. 37, the fuzzy sets ZO, PS, and PB in which the X axis for the fuzzy sets of deviation is in the positive quadrant are multiplied by 1.1 to increase by 10% as a specific scaling factor, for the X values of vertex coordinates of fuzzy sets in which the grade is 0 or 1.

Consequently, there is an enlargement in the positive direction of the X axis, and the enlarged fuzzy sets are updated as new fuzzy sets.

The response characteristics are monitored for every measurement step of gene analysis, and this updating is carried out on the current fuzzy sets when the overshoot value has exceeded 0.5° C. (specific value).

There is an upper limit to the updating, and this is when the X value of the vertex value of the PS set is 16.0.

Figure 38:
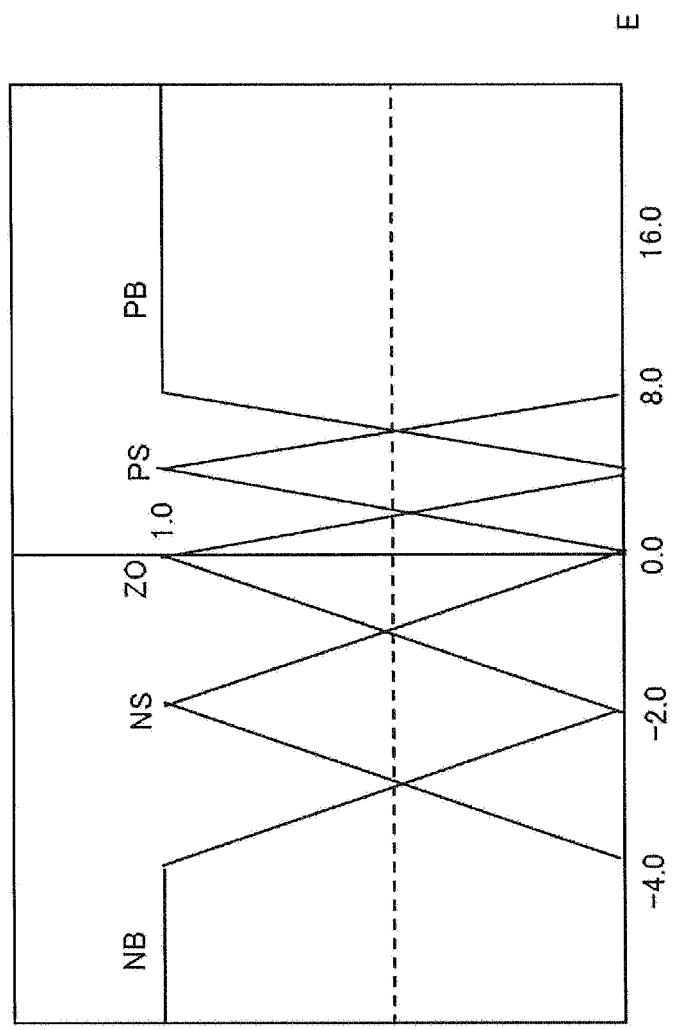
FIG. 38 shows fuzzy sets in the temperature control method in an embodiment of the present invention.

Also, the time axis response characteristics of the current temperature are monitored, and if the current temperature has not reached the target temperature (60° C. here) in at least a specific amount of time (3 minutes here), then the fuzzy sets ZO, PS, and PB in which the X axis of the fuzzy sets for deviation is in the positive quadrant are multiplied by 0.9, which is a specific scaling factor of less than 1, for X values of vertex coordinates of fuzzy sets in which the grade is 0 or 1, as shown in FIG. 38.

This causes a reduction in the positive direction of the X axis, and updates these reduced fuzzy sets as the new fuzzy sets.

The response characteristics are monitored for every measurement step of gene analysis, and this updating is carried out on the current fuzzy sets when the current temperature has not reached the target temperature (60° C. here) in at least a specific amount of time (3 minutes here).

There is a lower limit to the updating, and this is when the X value of the vertex value of the PS set is 0.8.

Figure 39:
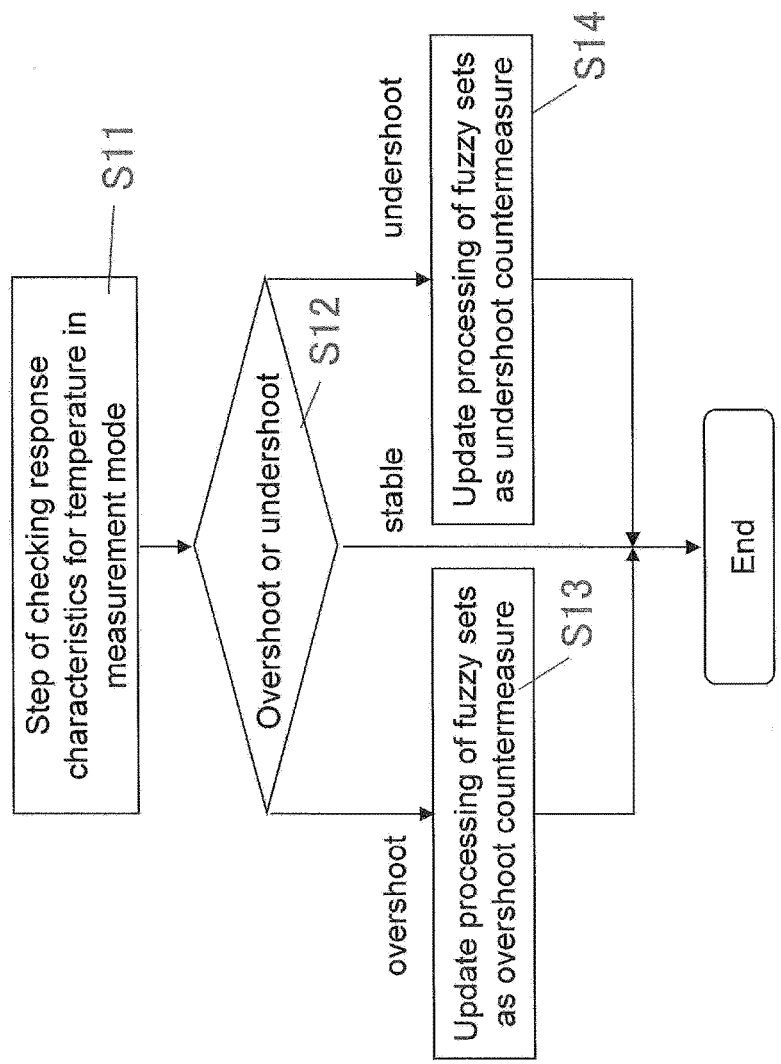
FIG. 39 is a flowchart of the temperature control method in an embodiment of the present invention.

FIG. 39 is a flowchart of the above processing.

First, in the measurement step of genetic analysis, a step of monitoring the response characteristics of temperature control is performed (S11).

Next, it is determined whether or not the overshoot value of these response characteristics has exceeded a specific value (0.5° C. here), or the current temperature has not reached the target temperature (60° C. here) in at least a specific amount of time (3 minutes here) (S12).

Then, if the overshoot value of these response characteristics has exceeded the specific value of 0.5° C., a step of updating the fuzzy sets (S13) is performed as an overshoot countermeasure.

On the other hand, if the current temperature has not reached the target temperature of 60° C. in at least the specific amount of time of 3 minutes, a step of updating the fuzzy sets (S14) is performed as an undershoot countermeasure.

That is, with the control method in this embodiment, in the first step (S11, S12), the time axis response of temperature is monitored, and it is determined whether or not the overshoot value has exceeded a specific value or the response rate of the response value is at least a specific length of time. Then, in the second step (S13, S14), the fuzzy sets ZO, PS, and PB in which the X axis of the fuzzy sets of deviation is in the positive quadrant are multiplied by a specific scaling factor for X values of vertex coordinates of fuzzy sets in which the grade is 0 or 1, and the fuzzy sets that have been enlarged or reduced in the positive direction of the X axis are updated as the new fuzzy sets.

Employing the above control method improves the response characteristics of temperature control, and therefore allow more accurate genetic analysis to be carried out.

(A)

An example was given in which a centrifugal fan was used as the fan 7 that blew air at the analysis receptacle 4, but the present invention is not limited to this. For example, an axial fan may be used instead of a centrifugal fan.

(B)

An example was given in which the heater 13, which heated air sent out by the fan 7, was provided in the interior of the fan 7, but the present invention is not limited to this. For example, the heater may be provided on the outside of the fan.

(C)

An example was given in which the analysis receptacle 4 was such that the first regions 32a and 32b, which were located farther away from the rotational axis center than the second regions 33a and 33b provided on a straight line, were formed in an arc shape, but the present invention is not limited to this.

For example, the contour shape of the sides where the first regions are disposed is not limited to being arc shaped, and may instead be linear.

Working Example

Figure 40:
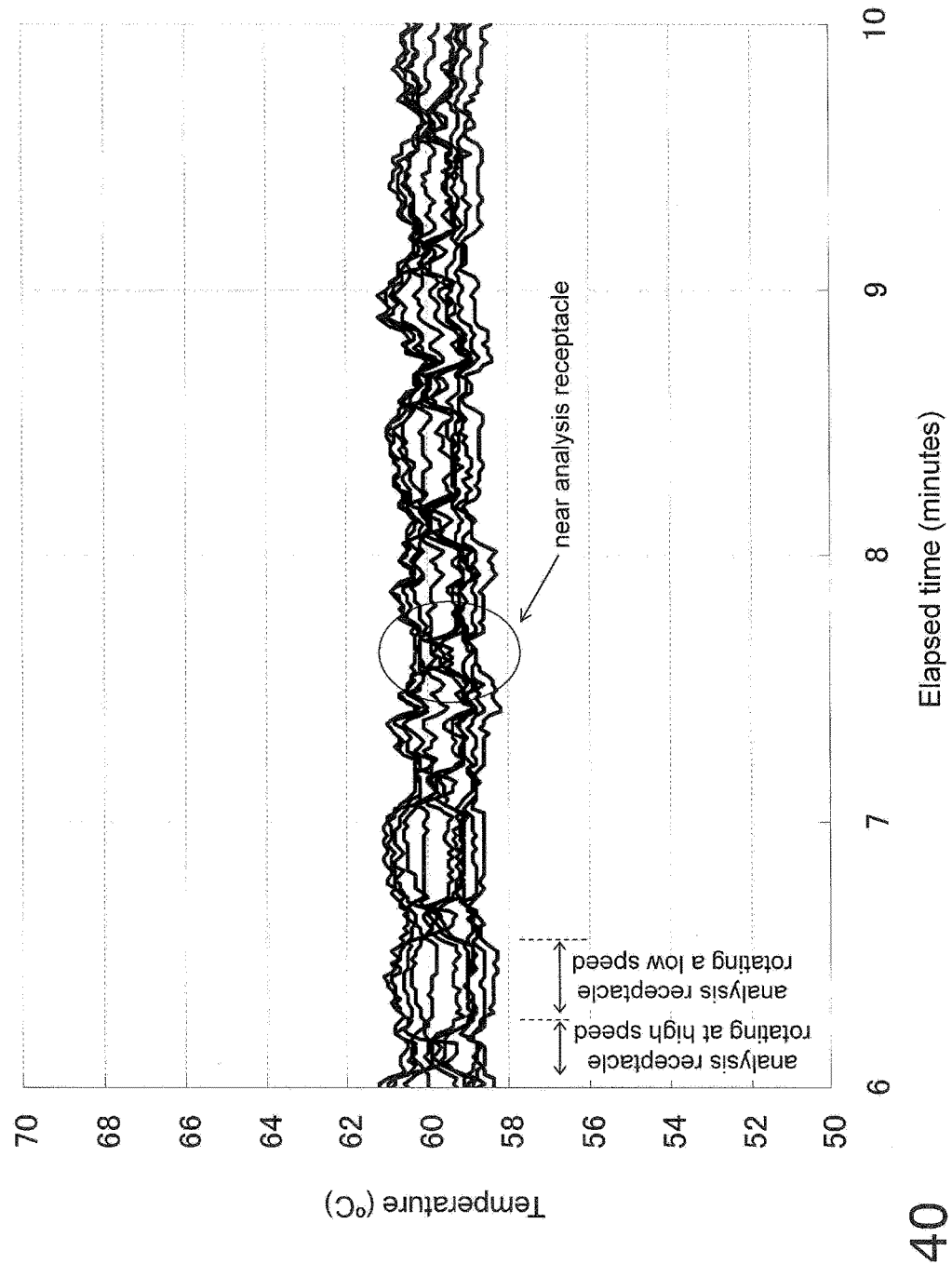
FIG. 40 is a graph of the experiment results in a working example of the present invention.

FIG. 40 shows the results of an actual experiment into the measurement results with a plurality of temperature sensors 14 installed in the analysis chamber 6, for the genetic analysis device described in the above embodiment. In this working example, the experiment was conducted under the following conditions.

10 seconds of high-speed rotation was alternated with 20 seconds of low-speed rotation.
High-speed rotation: 3000 rpm
Low-speed rotation: 240 rpm
Target temperature: 60° C.

Temperature control was performed so that 60° C. would be the average temperature reading for the four temperature sensors provided around a circle centered on the rotational axis center in the analysis receptacle 4.

As a result, as shown in FIG. 40, the measurement temperatures obtained from the four temperature sensors were found to fall within a range of 58 to 61° C.

Also, temperature variance was constant within the above range, during both the period in which the analysis receptacle 4 was rotated at high speed, and the period in which it was rotated at low speed.

Comparative Example

Figure 41:
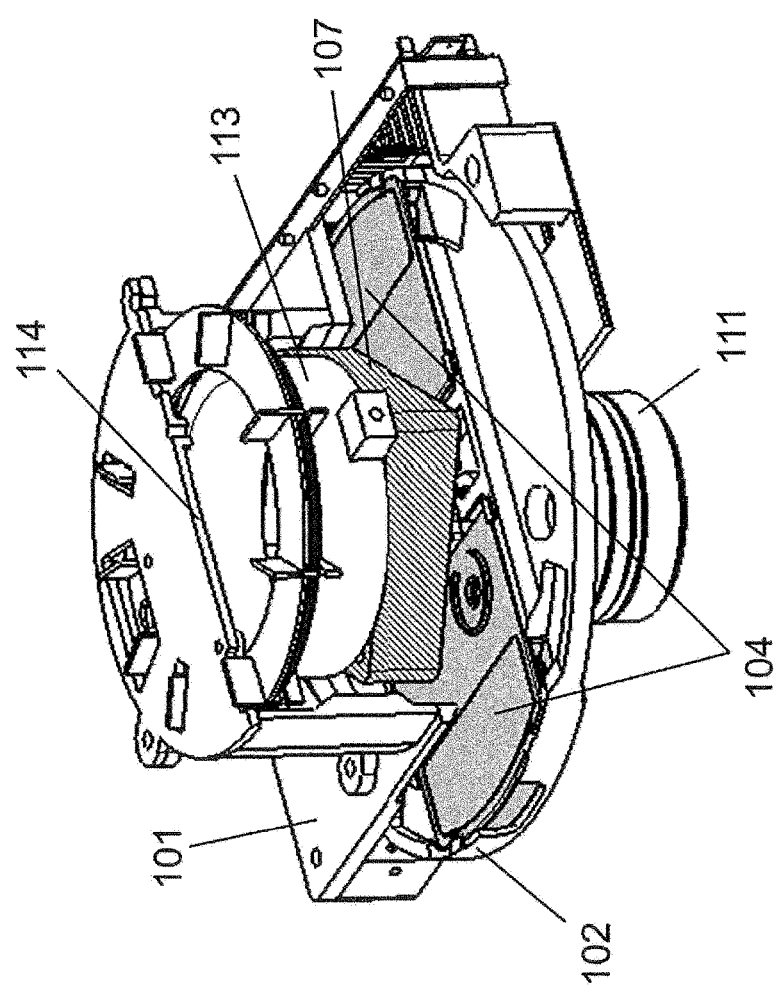
FIG. 41 is an oblique view of the configuration of the genetic analysis device pertaining to a comparative example of the present invention.
Figure 42:
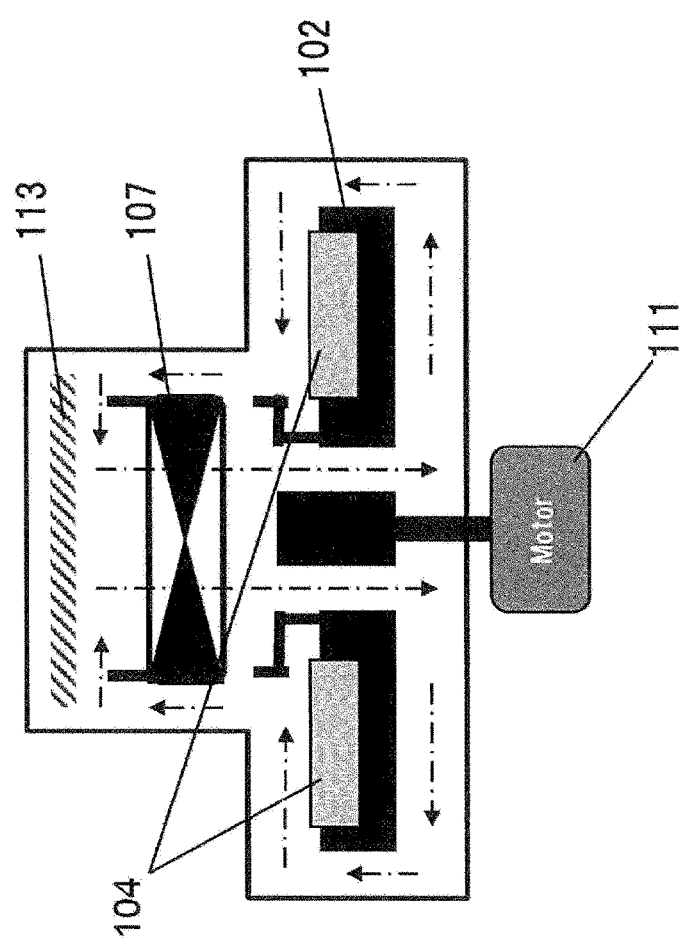
FIG. 42 is a simplified diagram of the internal configuration of the genetic analysis device in FIG. 41.

FIGS. 41 and 42 show the configuration of the genetic analysis device in a comparative example, with respect to the working example given above.

As shown in FIG. 41, the genetic analysis device in this comparative example comprises a main case 101, a tray 102, an analysis receptacle 104, a fan 107, a motor 111, a heater 113, and a temperature sensor 114.

The tray 102 and the analysis receptacle 104 are installed in an analysis chamber formed in the interior of the main case 101.

The fan 107 is provided at the top of the analysis chamber, and blows air downward toward the analysis chamber. As shown in FIG. 42, the air flow formed by the fan 107 escapes to the lower part of the analysis chamber through an opening formed in the center part of the analysis chamber, after which it goes from the sides of the analysis receptacle 104, through the top face side, and circulates back to the top part of the fan 107.

The motor 111 is provided at the bottom part of the main case 101, and rotates the tray 102 and the analysis receptacle 104 via a rotary shaft.

The heater 113 is disposed at the top part of the fan 107 inside the main case 101, and heats the air blown in by the fan 107.

Using the genetic analysis device in this comparative example and having the above configuration, an experiment was conducted under the following conditions.

10 seconds of high-speed rotation was alternated with 50 seconds of low-speed rotation.
High-speed rotation: 3000 rpm
Low-speed rotation: 230 rpm
Target temperature: 60° C.

Temperature control was performed so that 60° C. would be the average temperature reading, using a temperature sensor provided near the center of the heater 113.

Figure 43:
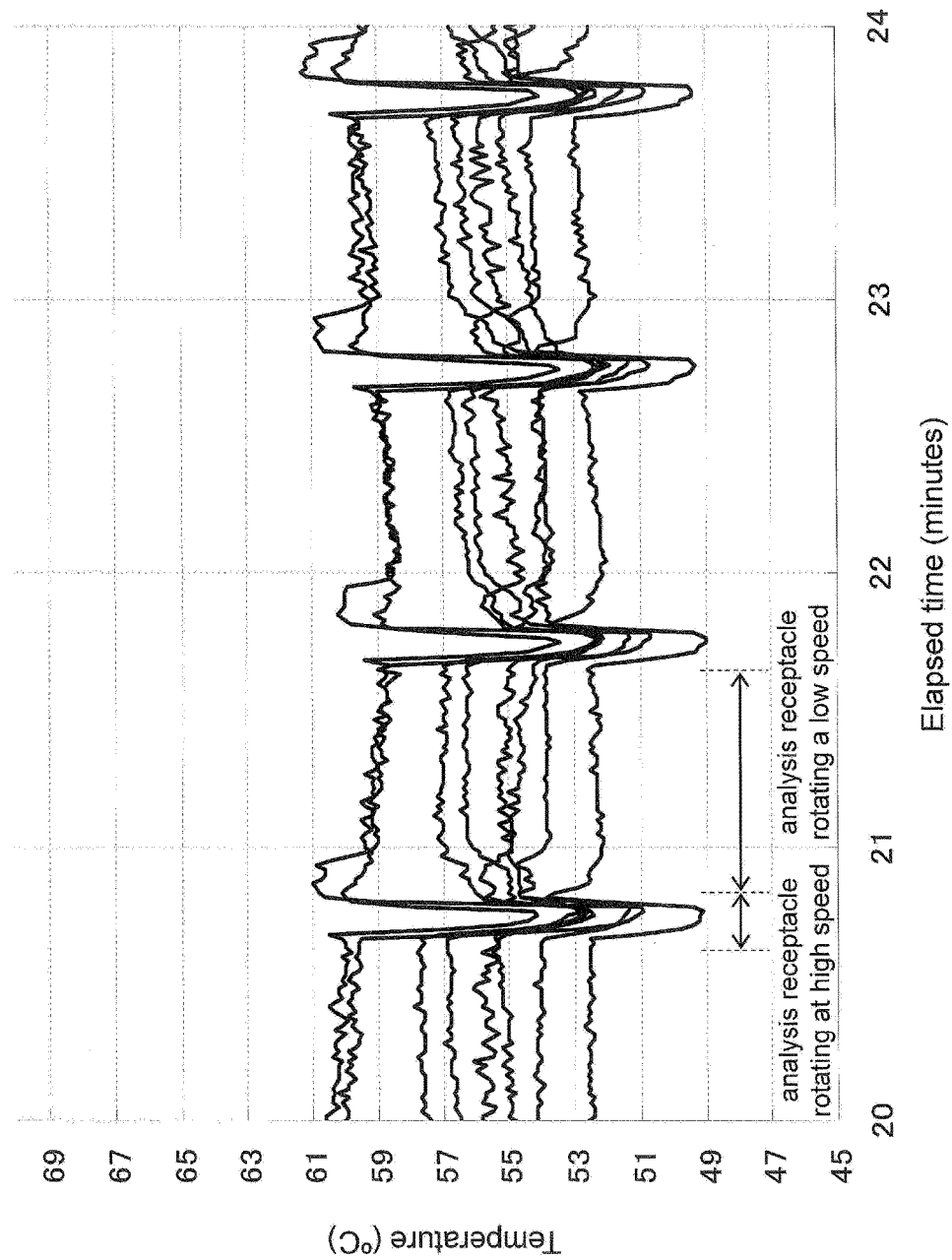
FIG. 43 is a graph of the experiment results for the genetic analysis device of the comparative example in FIG. 41.

As a result, as shown in FIG. 43, the measurement temperature obtained from the temperature sensor was found to vary over a range of 49 to 61° C.

In particular, the variance in temperature was found to be largest during the period in which the analysis receptacle 104 was rotated at high speed.

In the configuration of this comparative example, one possible reason why there was more temperature variance than with the configuration of the working example is that the rotation of the analysis receptacle 104 impedes the stirring of air by the fan 107, and during high-speed rotation the transmission of heat from the heater 113 to the area around the analysis receptacle 104 is not as good.

Conclusion

In light of the above results, it was found that with the configuration of this working example, the range of temperature variance can be reduced form 12° C. to 3° C. versus the results in this comparative example.

It was found from the above results that with the configuration of this working example, since the air is stirred in the portion where the analysis receptacle touches the air flow, there is extremely little temperature unevenness at the portion where the analysis receptacle touches the air flow. Thus, the effect that can be obtained is an improvement in analysis accuracy.

INDUSTRIAL APPLICABILITY

As discussed above, certain implementations of the present invention has the effect of allowing analysis accuracy to be improved, and as such is expected to find application in devices for analyzing genes and so forth.

The invention claimed is:

1. An analysis device, comprising:
an analysis chamber inside of which an analysis receptacle is positioned;
a fan positioned inside the analysis chamber and configured to blow air at the analysis receptacle so that the air circulates in a circular manner along a surface on which the analysis receptacle is positioned in the analysis chamber;
a heater configured to heat the air blown from the fan at the analysis receptacle; and
an analysis receptacle rotary driver positioned a specific distance away from the fan in a blowing direction of the fan inside the analysis chamber, and configured to rotate the analysis receptacle in a same direction as a direction of air flow formed by the fan,
wherein the analysis chamber is defined by linking a first round part that defines a cylindrical space in which the fan is housed, and a second round part that defines a cylindrical space in which the analysis receptacle rotary driver is housed, and wherein a radius of the second round part is larger than a radius of the first round part.

2. The analysis device according to claim 1, wherein the first round part is positioned around a circle having a center which is a rotational axis of the fan, and wherein the second round part is positioned around a circle having a center which is a rotational axis of the analysis receptacle rotary driver.

3. The analysis device according to claim 1, wherein the analysis chamber has an analysis receptacle insertion opening positioned at the second round part, and wherein an analysis receptacle loading tray is positioned so as to be able to move in and out of the analysis receptacle insertion opening.

* * * * *